US012616361B2

(12) United States Patent
Rask et al.

(10) Patent No.: US 12,616,361 B2
(45) Date of Patent: May 5, 2026

(54) MEDICAL DEVICE INCLUDING A TUBE

(71) Applicant: AMBU A/S, Ballerup (DK)

(72) Inventors: Jesper Domino Rask, Copenhagen S
(DK); Morten Sørensen, Ballerup
(DK); Martin Lund Størup, Brønshøj
(DK); Lars Ulrik Nielsen, Virum (DK)

(73) Assignee: AMBU A/S, Ballerup (DK)

( * ) Notice: Subject to any disclaimer, the term of this
patent is extended or adjusted under 35
U.S.C. 154(b) by 332 days.

(21) Appl. No.: 18/044,491

(22) PCT Filed: Aug. 23, 2021

(86) PCT No.: PCT/EP2021/073278
§ 371 (c)(1),
(2) Date: Mar. 8, 2023

(87) PCT Pub. No.: WO2022/063502
PCT Pub. Date: Mar. 31, 2022

(65) Prior Publication Data
US 2023/0355085 A1     Nov. 9, 2023

(30) Foreign Application Priority Data

Sep. 22, 2020    (DK) ........................... PA 2020 70622

(51) Int. Cl.
*A61B 1/05*          (2006.01)
*A61B 1/015*         (2006.01)
(52) U.S. Cl.
CPC ................ *A61B 1/05* (2013.01); *A61B 1/015*
(2013.01)
(58) Field of Classification Search
CPC .. G02B 23/2476; G02B 23/2484; A61B 1/05;
A61B 1/051; A61B 1/267
See application file for complete search history.

(56) References Cited

U.S. PATENT DOCUMENTS 5,499,625 A     3/1996  Frass et al.
5,725,476 A     3/1998  Yasui et al.
(Continued)

FOREIGN PATENT DOCUMENTS

WO     2017205357 A1    11/2017

OTHER PUBLICATIONS

First technical report in Denmark Patent Application No. PA 2020
70621, dated Aug. 25, 2021, 9 pgs.
(Continued)

*Primary Examiner* — Alexandra L Newton
(74) *Attorney, Agent, or Firm* — Faegre Drinker Biddle &
Reath LLP

(57)          ABSTRACT

The tube has a first lumen with a proximal end and an open
distal end to be placed inside a body cavity. An outer wall
encloses the first lumen and a camera lumen. A camera
module (10) is arranged in the camera lumen at a distal end
thereof so that the camera module is positioned adjacent the
distal end of the first lumen. An image transmission cable
(13) attached to the camera module extends through the
camera lumen to connect to an image display device. The
camera module is fixed in the camera lumen by means of a
camera housing (14) including a tubular housing part (17)
surrounding the camera module and a distal end wall (18).
The tubular housing part and the distal end wall are inte-
grally moulded and form one single housing element (19).
The tubular housing part fits tightly into the camera lumen
of the tube.

26 Claims, 20 Drawing Sheets

(56) References Cited

U.S. PATENT DOCUMENTS

| | | | |
|---|---|---|---|
| 5,904,648 | A | 5/1999 | Arndt et al. |
| 6,079,409 | A | 6/2000 | Brain |
| 6,142,144 | A | 11/2000 | Pacey |
| 6,248,060 | B1 | 6/2001 | Buess et al. |
| 6,533,722 | B2 | 3/2003 | Nakashima |
| 6,543,447 | B2 | 4/2003 | Pacey |
| 6,655,377 | B2 | 12/2003 | Pacey |
| 6,923,176 | B2 | 8/2005 | Ranzinger |
| 6,929,600 | B2 | 8/2005 | Hill |
| 7,013,899 | B2 | 3/2006 | Alfery et al. |
| 7,201,168 | B2 | 4/2007 | McGrail et al. |
| 7,233,820 | B2 | 6/2007 | Gilboa |
| 7,458,375 | B2 | 12/2008 | Schwartz et al. |
| 7,530,946 | B2 | 5/2009 | Hartwick |
| 7,658,708 | B2 | 2/2010 | Schwartz et al. |
| 7,921,847 | B2 | 4/2011 | Totz |
| 7,938,119 | B2 | 5/2011 | Chen et al. |
| 7,998,062 | B2 | 8/2011 | Gilboa |
| 8,038,606 | B2 | 10/2011 | Otawara |
| 8,998,798 | B2 | 4/2015 | Hayman et al. |
| 9,155,854 | B2 | 10/2015 | Hayman et al. |
| 9,283,342 | B1 | 3/2016 | Gardner |
| 9,332,891 | B2 | 5/2016 | Vazales et al. |
| 9,357,905 | B2 | 6/2016 | Molnar et al. |
| 9,415,179 | B2 | 8/2016 | Molnar |
| 9,572,946 | B2 | 2/2017 | Chun |
| 9,579,012 | B2 | 2/2017 | Vazales et al. |
| 9,603,515 | B2 | 3/2017 | Zocca et al. |
| 9,662,466 | B2 | 5/2017 | Gunday et al. |
| 9,750,913 | B2 | 9/2017 | Schwartz et al. |
| 9,788,755 | B2 | 10/2017 | Hayman et al. |
| 9,801,535 | B2 | 10/2017 | Turnbull |
| 9,820,642 | B2 | 11/2017 | Law et al. |
| 9,854,962 | B2 | 1/2018 | McGrail et al. |
| 9,855,111 | B2 | 1/2018 | Vazales et al. |
| 9,888,832 | B2 | 2/2018 | Schwartz et al. |
| 9,907,624 | B2 | 3/2018 | Vazales et al. |
| 9,918,618 | B2 | 3/2018 | Molnar |
| 9,949,629 | B2 | 4/2018 | Gardner |
| 10,149,602 | B2 * | 12/2018 | Daher ..................... A61B 1/12 |
| 10,245,402 | B2 | 4/2019 | Daher et al. |
| 10,406,309 | B2 | 9/2019 | Daher |
| 10,478,054 | B2 | 11/2019 | Nave et al. |
| 10,888,679 | B2 | 1/2021 | Daher et al. |
| 2001/0017135 | A1 | 8/2001 | Cook |
| 2005/0129592 | A1 | 6/2005 | Kihara et al. |
| 2005/0268917 | A1 | 12/2005 | Boedeker et al. |
| 2006/0025650 | A1 | 2/2006 | Gavriely |
| 2008/0188715 | A1 | 8/2008 | Fujimoto |
| 2008/0200764 | A1 | 8/2008 | Okada |
| 2009/0105538 | A1 * | 4/2009 | Van Dam ........... A61B 1/00105 |
| | | | 345/173 |
| 2009/0253964 | A1 | 10/2009 | Miyamoto |
| 2011/0197888 | A1 | 8/2011 | Deutsch et al. |
| 2011/0275894 | A1 | 11/2011 | Mackin |
| 2011/0313347 | A1 | 12/2011 | Zocca et al. |
| 2011/0315147 | A1 | 12/2011 | Wood et al. |
| 2012/0065469 | A1 | 3/2012 | Allyn et al. |
| 2012/0172664 | A1 | 7/2012 | Hayman et al. |
| 2012/0172665 | A1 | 7/2012 | Allyn et al. |
| 2012/0226100 | A1 | 9/2012 | Greenburg et al. |
| 2012/0259173 | A1 | 10/2012 | Waldron et al. |
| 2012/0298111 | A1 | 11/2012 | Wood et al. |
| 2012/0302833 | A1 | 11/2012 | Hayman et al. |
| 2013/0158351 | A1 | 6/2013 | Daher et al. |
| 2013/0269703 | A1 | 10/2013 | Wood et al. |
| 2013/0303849 | A1 | 11/2013 | Allyn et al. |
| 2013/0317339 | A1 | 11/2013 | Waldstreicher et al. |
| 2013/0324798 | A1 | 12/2013 | Molnar et al. |
| 2013/0338436 | A1 | 12/2013 | Dresher et al. |
| 2014/0005480 | A1 | 1/2014 | Wagner et al. |
| 2014/0024893 | A1 | 1/2014 | Dorsey et al. |
| 2014/0024895 | A1 | 1/2014 | Allyn |
| 2014/0031622 | A1 | 1/2014 | Daher |
| 2014/0033455 | A1 | 2/2014 | Vazales et al. |
| 2014/0073853 | A1 | 3/2014 | Swisher et al. |
| 2014/0076326 | A1 | 3/2014 | Pol |
| 2014/0094651 | A1 | 4/2014 | Allyn et al. |
| 2014/0094652 | A1 | 4/2014 | Lewis et al. |
| 2014/0094653 | A1 | 4/2014 | Lewis et al. |
| 2014/0150782 | A1 | 6/2014 | Vazales et al. |
| 2014/0221921 | A1 | 8/2014 | Gilboa |
| 2014/0309494 | A1 | 10/2014 | Molnar |
| 2015/0099927 | A1 | 4/2015 | Sadoughi |
| 2015/0126808 | A1 | 5/2015 | Roze |
| 2015/0133741 | A1 | 5/2015 | Gill |
| 2015/0174352 | A1 | 6/2015 | Hayman et al. |
| 2015/0190044 | A1 | 7/2015 | Livnat |
| 2015/0223668 | A1 | 8/2015 | Gilboa et al. |
| 2015/0305596 | A1 | 10/2015 | Oskin et al. |
| 2015/0305650 | A1 | 10/2015 | Hunter et al. |
| 2015/0378144 | A1 | 12/2015 | Handte et al. |
| 2016/0000303 | A1 | 1/2016 | Klein et al. |
| 2016/0030693 | A1 | 2/2016 | Nakatate et al. |
| 2016/0038008 | A1 | 2/2016 | Molnar |
| 2016/0038014 | A1 | 2/2016 | Molnar |
| 2016/0051221 | A1 | 2/2016 | Dickhans et al. |
| 2016/0081534 | A1 | 3/2016 | Lisogurski et al. |
| 2016/0101253 | A1 | 4/2016 | Alahmadi |
| 2016/0106308 | A1 | 4/2016 | Field |
| 2016/0206188 | A1 * | 7/2016 | Hruska ................ A61B 1/0684 |
| 2016/0206189 | A1 | 7/2016 | Nearman et al. |
| 2016/0227991 | A1 | 8/2016 | Hayut et al. |
| 2016/0256646 | A1 | 9/2016 | Vazales |
| 2016/0262603 | A1 | 9/2016 | Molnar |
| 2017/0119494 | A1 | 5/2017 | Vazales et al. |
| 2017/0232216 | A1 | 8/2017 | Nave et al. |
| 2018/0084971 | A1 | 3/2018 | Truckai et al. |
| 2019/0083728 | A1 | 3/2019 | Nawn et al. |
| 2019/0246873 | A1 | 8/2019 | Lu et al. |
| 2020/0288953 | A1 | 9/2020 | Sørensen et al. |
| 2020/0297193 | A1 | 9/2020 | Takahashi et al. |
| 2020/0352650 | A1 | 11/2020 | Chu et al. |
| 2021/0068625 | A1 | 3/2021 | Shin et al. |

OTHER PUBLICATIONS

First technical report in Denmark Patent Application No. PA 2020 70622, dated Mar. 15, 2021, 8 pgs.

International Search Report and Written Opinion in International Application No. PCT/EP2021/073278, mailed Nov. 30, 2021, 14 pgs.

International Search Report and Written Opinion in International Application No. PCT/EP2021/073279, mailed Dec. 3, 2021, 14 pgs.

* cited by examiner

MEDICAL DEVICE INCLUDING A TUBE

CROSS-REFERENCE TO RELATED APPLICATIONS

This application is a National Phase entry under 35 U.S.C. § 371 of International Application No. PCT/EP2021/073278, filed Aug. 23, 2021, which claims the benefit of and priority from Denmark Patent Application No. PA 2020 70622, filed Sep. 22, 2020; said applications are incorporated by reference herein in their entirety.

TECHNICAL FIELD

The present disclosure relates to a medical device including a tube having at least a first lumen and a dedicated camera lumen, the first lumen having a proximal end and an open distal end, the distal end being adapted to be placed inside a body cavity during use of the medical device, the tube having an outer wall enclosing at least the first lumen and the camera lumen, the camera lumen having a proximal end and a distal end, a camera module including at least an image sensor and one or more light sources being arranged in the camera lumen at the distal end thereof so that the camera module is positioned adjacent the distal end of the first lumen, and an image transmission cable attached to the camera module extending through at least part of the camera lumen in order to connect to an image display device.

BACKGROUND

EP 2 754 384 B1 (Ambu A/S) discloses an endobronchial tube which contains an integrated camera and light source and a cleaning nozzle arrangement disposed within a dedicated peripheral lumen within the tube's wall. The endobronchial tube may for instance be made of plastic, rubber, polymers or silicone. In the illustrated embodiment, the endobronchial tube is a double lumen tube including a tracheal lumen and a bronchial lumen. The camera is arranged in said peripheral lumen of the tube at the distal end of the tracheal lumen in order to visualise the tracheal carina and the distal end of the bronchial lumen during its insertion into the left or right bronchus. However, in known solutions, the fitting of a camera module in said dedicated peripheral lumen may be cumbersome. In a manual procedure, firstly, said peripheral lumen may be dilated in order to fit the camera module, and, secondly, the camera module may be fixed in the lumen by means of glue. Following this procedure, correct positioning of the camera module in the peripheral lumen may be difficult. Furthermore, in a double lumen tube, it may be a disadvantage that the angle of view of the camera may be restricted in such a way that the captured image shows to a large degree the distal end of the bronchial lumen rather than the anatomy of the patient.

An object of the present disclosure is to provide a medical device being easier to assemble correctly.

SUMMARY

In view of this object, the camera module is fixed in the camera lumen by means of a camera housing extending in a longitudinal direction and having a proximal end and a distal end, in that the camera housing includes a tubular housing part at least partly surrounding the camera module and a distal end wall, in that the tubular housing part and the distal end wall are integrally moulded and form one single housing element, and in that the tubular housing part fits tightly into the camera lumen of the tube.

Thereby, precise mounting of a camera module in the camera lumen may be facilitated in that a tight fit between the tubular housing part and the camera lumen may ensure precise positioning of the camera module in the lumen without any adjustments being necessary. In particular, dilatation of the camera lumen of the tube in order to mount the camera module in the camera lumen may not be necessary.

In an embodiment, the camera housing includes a support structure for the camera module, the support structure has a proximal end and a distal end, the proximal end of the support structure has a tubular end part arranged inside the tubular housing part of the camera housing, the image transmission cable extends through the tubular end part of the support structure, and the distal end of the support structure is engaged with the camera module. Thereby, the arrangement of the camera module in the camera housing may be facilitated in that the tubular end part of the support structure may fit inside the tubular housing part and thereby ensure correct positioning of the support structure with the camera module inside the camera housing. Thereby, precise mounting of the camera module in the camera lumen may be further facilitated. Furthermore, the tubular end part of the support structure may seal against the tubular housing part, and the image transmission cable may seal against an inside of the tubular end part. Thereby, the camera module may be protected against the environment.

In an embodiment, the tubular end part of the support structure has an outer face being glued to an inner face of the tubular part of the camera housing. Thereby, the tubular end part of the support structure may seal even better against the tubular housing part.

In an embodiment, the outer face of the tubular end part of the support structure and/or the inner face of the tubular housing part of the camera housing are/is tapered or conical so that a gap for glue is formed, a cross-section of said gap generally decreasing in the direction from the proximal end to the distal end of the support structure. Thereby, correct application of glue may be ensured. Capillary effects may ensure that glue enters the gap and the decreasing cross-section of the gap may serve to avoid that glue enters too far inside of the camera housing.

In an embodiment, the outer face of the tubular end part of the support structure and/or the inner face of the tubular part of the camera housing are/is provided with a number of ribs distributed in the circumferential direction of the outer face and/or the inner face. The ribs may ensure that the support structure is centred inside the camera housing such that the two parts can be glued together by utilizing capillary effects.

In an embodiment, the ribs only extend at a distal end of the tubular end part of the support structure. Thereby, entrance of glue into the gap may be facilitated.

In an embodiment, said ribs include two pivot forming ribs arranged diametrically opposite of the tubular end part of the support structure and/or of the tubular part of the camera housing and together providing a relatively tight fit with the corresponding outer face or inner face, and said ribs further include at least two distance ribs distributed peripherally about the tubular end part of the support structure and/or of the tubular part of the camera housing and together providing a relatively loose fit with the corresponding outer face or inner face. The two pivot forming ribs arranged diametrically opposite of the tubular end part of the support structure and/or of the tubular part of the camera housing may ensure that the support structure may pivot about an axis generally extending through said pivot forming ribs during the insertion of the support structure into the tubular part of the camera housing. Thereby, the distal end of the support structure may better engage the camera module in a flexible way so that the camera module may be guided into its correct position in the camera housing.

In an embodiment, the distal end of the support structure is provided with two spaced tabs arranged generally symmetrically about a plane extending through said two pivot forming ribs, and the two spaced tabs are adapted to abut the camera module. Thereby, both spaced tabs may tend to engage the camera module during its insertion into the camera housing, thereby even better ensuring that the camera module may be guided into its correct position in the camera housing.

In an embodiment, the support structure includes an elongated part having generally semi-circular cross-section, and the elongated part connects the proximal end of the support structure with the two spaced tabs. Thereby, the semi-circular support wall may mate with the interior structure of the camera housing.

In an embodiment, the elongated part is provided with a peripherally extending recess facing the inner face of the tubular part of the camera housing next to the tubular end part of the support structure. The peripherally extending recess may stop the glue from moving further into the camera housing. This way it may be possible to control the amount of glue needed to ensure a good sealing effect.

In an embodiment, the tubular end part of the support structure has an inner face being glued to an outer face of the image transmission cable. Thereby, a good sealing effect may be achieved.

In an embodiment, the inner face of the tubular end part of the support structure is tapered or conical so that a gap for glue is formed, a cross-section of said gap generally decreasing in the direction from the proximal end to the distal end of the support structure. Thereby, correct application of glue may be ensured. Capillary effects may ensure that glue enters the gap and the decreasing cross-section of the gap may serve to avoid that glue enters too far inside of the camera housing.

In an embodiment, the inner face of the tubular end part of the support structure is provided with a number of ribs distributed in the circumferential direction of the inner face. The ribs may ensure that image transmission cable is centred inside the tubular end part of the support structure such that the two parts can be glued together by utilizing capillary effects.

In an embodiment, the support structure or the inner face of the tubular part of the camera housing has a guide rib extending in the longitudinal direction of the camera housing, the corresponding one of the support structure and the inner face of the tubular part of the camera housing has a groove extending in the longitudinal direction of the camera housing, and the guide rib is adapted to slide in the groove. Thereby, the tubular part of the camera housing may be configured to receive and guide the camera module support structure. In this way, it may be ensured that the camera module is guided to the correct rotational orientation inside the camera housing.

In an embodiment, the camera module is arranged extending from the distal end of the support structure, the inner face of the tubular part of the camera housing is provided with the guide rib, and the guide rib is wedge-formed at the distal end of the camera housing in order to guide the camera module. Thereby, it may even better be ensured that the camera module is guided into its correct position during the last part of the insertion procedure of the support structure.

In an embodiment, the inner face of the tubular part of the camera housing is provided with the guide rib, the elongated part is provided with the groove extending in the longitudinal direction of the camera housing, the groove is arranged symmetrically about the plane extending through said two pivot forming ribs, and the guide rib has a loose fit in the groove. The loose fit of the guide rib in the groove and the symmetric arrangement of the groove about said plane may even better ensure that the support structure may pivot about an axis generally extending through said pivot forming ribs during the insertion of the support structure into the tubular part of the camera housing. Thereby, the distal end of the support structure may better engage the camera module in a flexible way so that the camera module may be guided into its correct position in the camera housing.

In an embodiment, a number of guide tabs are distributed in the circumferential direction of the inner face of the tubular part of the camera housing at the distal end wall of the camera housing, the guide tabs are provided on the inner face of the tubular part and/or on the distal end wall, and the guide tabs are arranged to guide the camera module during its insertion into the camera housing. Thereby, it may even better be ensured that the camera module may be guided into its correct position in the camera housing during its final displacement into the tubular housing part of the camera housing.

In an embodiment, the distal end wall of the camera housing has a recess in which at least a portion of a lens barrel of the camera module is inserted. Thereby, correct positioning of the lens barrel of the camera module may be ensured, but also the optical properties of the image captured by the camera module may be improved. As an alternative to the recess, the distal end wall may be provided with a through-hole the lens barrel of the camera module is positioned. The camera module would then need to be glued and sealed towards the edge of the through-hole.

In an embodiment, the camera housing includes a proximal portion arranged at a proximal end of the tubular housing part, the proximal portion has a proximal end and a distal end and a tapering part arranged between the proximal end and the distal end, and an outer diameter of the proximal end is smaller than an outer diameter of the distal end. Thereby, the camera housing may be mounted in the dedicated camera lumen of the tube by first threading the image transmission cable into the camera lumen from the distal end to the proximal end. The tapered part of the proximal portion of the camera housing may make it much easier to push the camera housing into the camera lumen of the tube which may be made of a soft/flexible polymer material. Thereby, dilatation of the camera lumen of the tube in order to mount the camera module in the camera lumen may be even less necessary.

In an embodiment, the tubular housing part has an outer cylindrical surface, and the outer diameter of the distal end of the proximal portion corresponds to an outer diameter of the outer cylindrical surface. Thereby, insertion of the camera housing into the camera lumen of the tube may be even further facilitated.

In an embodiment, the proximal portion is a separate element attached to the tubular housing part. Thereby, assembly of the camera housing may be facilitated.

In an embodiment, the distal end of the proximal portion has a number of protrusions distributed in its circumferential direction and abutting the proximal end of the tubular part, and the tubular part and the proximal portion are connected by means of glue. The number of protrusions may ensure an appropriate gap for glue between the remaining part of the distal end of the proximal portion and the proximal end of the tubular part.

In an embodiment, the proximal end of the tubular part has a number of protrusions distributed in its circumferential direction and abutting the distal end of the proximal portion, and the tubular part and the proximal portion are connected by means jof glue. The number of protrusions may ensure an appropriate gap for glue between the remaining part of the proximal end of the tubular part and the distal end of the proximal portion.

In an embodiment, the image transmission cable is retained inside of the proximal portion. Thereby, a strain relief for the image transmission cable may be ensured. Thereby, a pull relief may be provided for the image transmission cable so that the user does not inadvertently pull the cable apart from the camera module.

In an embodiment, a crimp is fixed on the image transmission cable inside the proximal portion. Thereby, in a simple manner, a pull relief may be provided for the image transmission cable so that the user does not inadvertently pull the cable apart from the camera module.

In a structurally particularly advantageous embodiment, the first lumen and the camera lumen, and an optional second lumen, are co-extruded to form the tube.

In a structurally particularly advantageous embodiment, the outer wall of the tube is generally ring-formed and surrounds at least the first lumen, and the camera lumen is formed in the material of the outer wall between an inner surface and an outer surface of the outer wall.

In a structurally particularly advantageous embodiment, the outer wall of the tube further surrounds at least part of a second lumen having a proximal end and an open distal end, and the first lumen and the second lumen are separated by means of a partition wall.

In a structurally particularly advantageous embodiment, the camera lumen is formed in the material of the outer wall at a position where the partition wall is connected to the outer wall.

In a structurally particularly advantageous embodiment, the outer wall of the tube surrounds the first lumen and a second lumen, the first lumen and the second lumen are separated by means of a partition wall, and the camera lumen is formed at the outer wall at a position where the partition wall is connected to the outer wall.

In a structurally particularly advantageous embodiment, the first lumen and the second lumen are symmetrically arranged about the partition wall and in relation to the camera lumen.

In an embodiment, the tubular housing part of the camera housing has a cylindrical outer surface having a central axis of symmetry, and a lens barrel of the camera module is eccentrically arranged in relation to the cylindrical outer surface of the tubular housing part. Thereby, the transverse position of the camera in the dedicated camera lumen of the tube may be adapted according to requirements by adapting the rotational position of the camera housing in the dedicated camera lumen of the tube. Thereby, the image captured by the camera may be influenced.

In an embodiment, a central axis of the lens barrel of the camera module is displaced in relation to the central axis of symmetry of the cylindrical outer surface of the tubular housing part of the camera housing in a direction so that the lens barrel is closer to the first lumen than to the second lumen. Thereby, in the case that the second lumen extends further distally than the first lumen, it may be ensured that the viewing angle of the camera covers relatively more of the surroundings of the tube than it covers of the part of the tube enclosing the second lumen distally of the first lumen. Thereby, in particular in the case of the medical device being a double lumen endotracheal tube having a first lumen in the form of a tracheal lumen and a second lumen in the form of a bronchial lumen, it may be ensured that the image captured by the camera module shows more of the anatomy and less of a tubing of a bronchial lumen with inflatable cuff inserted into the bronchus.

In an embodiment, the medical device is a catheter.

In an embodiment, the medical device is an airway device.

In an embodiment, the medical device is a double lumen endotracheal tube having a first lumen in the form of a tracheal lumen and a second lumen in the form of a bronchial lumen, the first lumen and the second lumen extend together from the proximal end of the first lumen to the distal end of the first lumen, and the second lumen extends beyond the distal end of the first lumen to a distal end of the second lumen.

In an embodiment, the double lumen endotracheal tube has a first inflatable cuff arranged proximally the open distal end of the first lumen and a second inflatable cuff arranged proximally the open distal end of the second lumen.

In an embodiment, the medical device is a single lumen endotracheal tube.

In an embodiment, the single lumen endotracheal tube has a first inflatable cuff arranged proximally the open distal end of the first lumen.

BRIEF DESCRIPTION OF THE DRAWINGS

The disclosure will now be explained in more detail below by means of examples of embodiments with reference to the very schematic drawing, in which.

DETAILED DESCRIPTION

Figure 1:
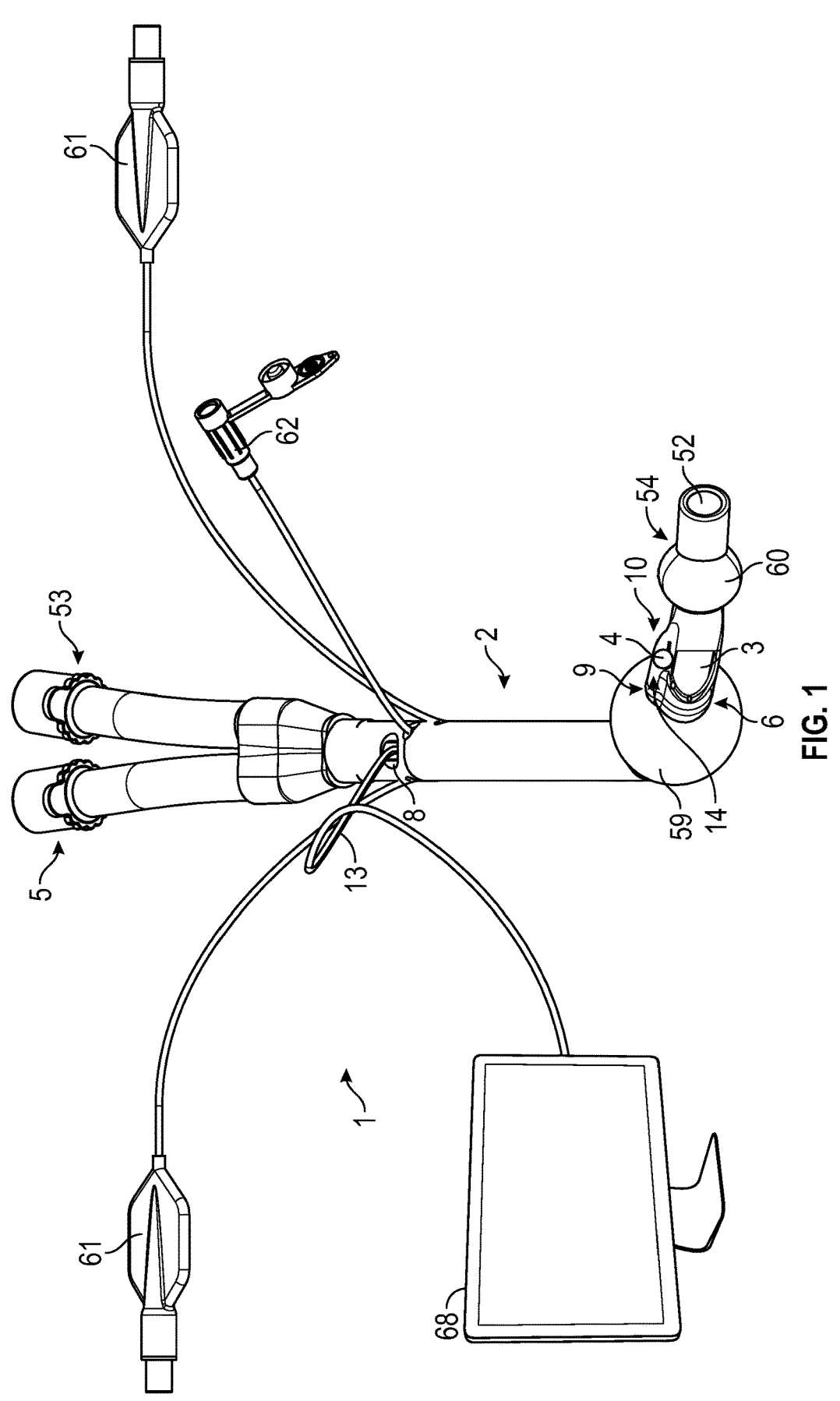
FIG. 1 is a perspective view of a double lumen endotracheal tube according to the present disclosure.

FIG. 1 illustrates a medical device according to the present disclosure in the form of a double lumen endotracheal tube 2 having a first lumen 3 in the form of a tracheal lumen and a second lumen 52 in the form of a bronchial lumen. A double lumen endotracheal tube as such is a well-known medical device and the use thereof is well-known to the skilled person. The first lumen 3 and the second lumen 52 extend together from the proximal end 5 of the first lumen 3 to the distal end 6 of the first lumen 3, and the second lumen 52 extends beyond the distal end 6 of the first lumen 3 to a distal end 54 of the second lumen 52. The double lumen endotracheal tube has a first inflatable cuff 59 arranged proximally the open distal end 6 of the first lumen 3 and a second inflatable cuff 60 arranged proximally the open distal end 54 of the second lumen 52. The first and second inflatable cuffs 59, 60 may be inflated in a well-known manner via a pilot balloon 61 provided with a one-way valve.

In use, the first inflatable cuff 59 is arranged in the trachea and the second inflatable cuff 60 is arranged in the left or right bronchus. Thereby, each bronchus may be ventilated separately in a well-known manner. The endotracheal tube may for instance be made of plastic, rubbers, e.g. butyl rubber, natural rubber or nitrile rubber, latex, neoprene, isoprene, polymers or silicones. The endotracheal tube may be made of Poly vinyl chloride (PVC) (with plasticizer), Thermoplastic elastomer (TPE), e.g. Styrene ethylene buty-lene styrene (SEBS), Styrene butylene styrene (SBS), Thermoplastic Polyurethanes (TPU) or Thermoplastic vulcani-zates (TPV). Most TPVs are binary blends of polyolefins and thermoplastic diene elastomers. Other elastomers sometimes used in TPVs include butyl rubber, natural rubber or nitrile rubber blended with iPP. Alternatively, blends of one or more of these materials may be used for producing the medical device, such as a catheter or endotracheal tube.

The endotracheal tube may be a single use product. The different lumens may be co-extruded in the tube 2.

Figure 2:
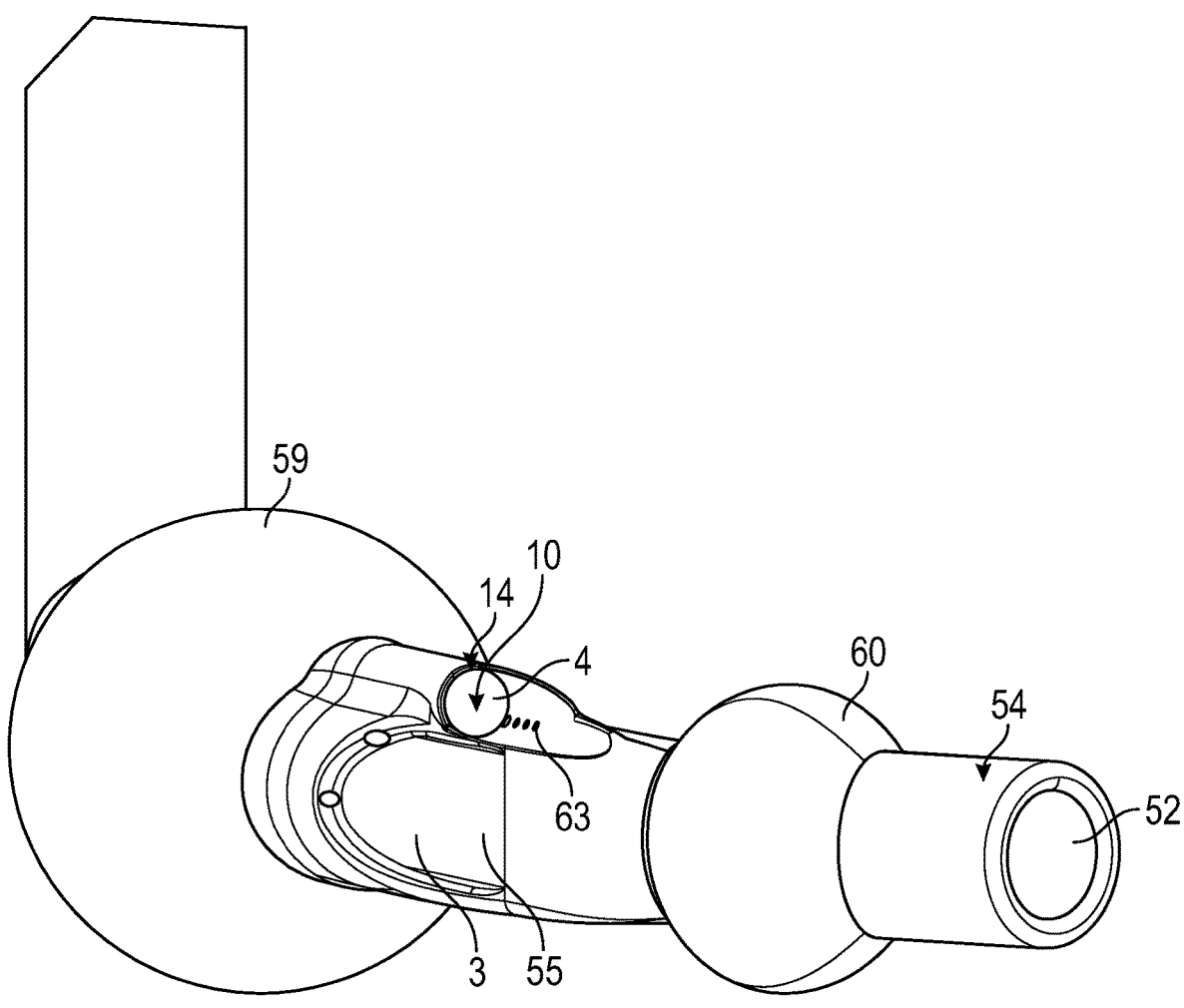
FIG. 2 illustrates, on a larger scale, a detail of FIG. 1.
Figure 3:
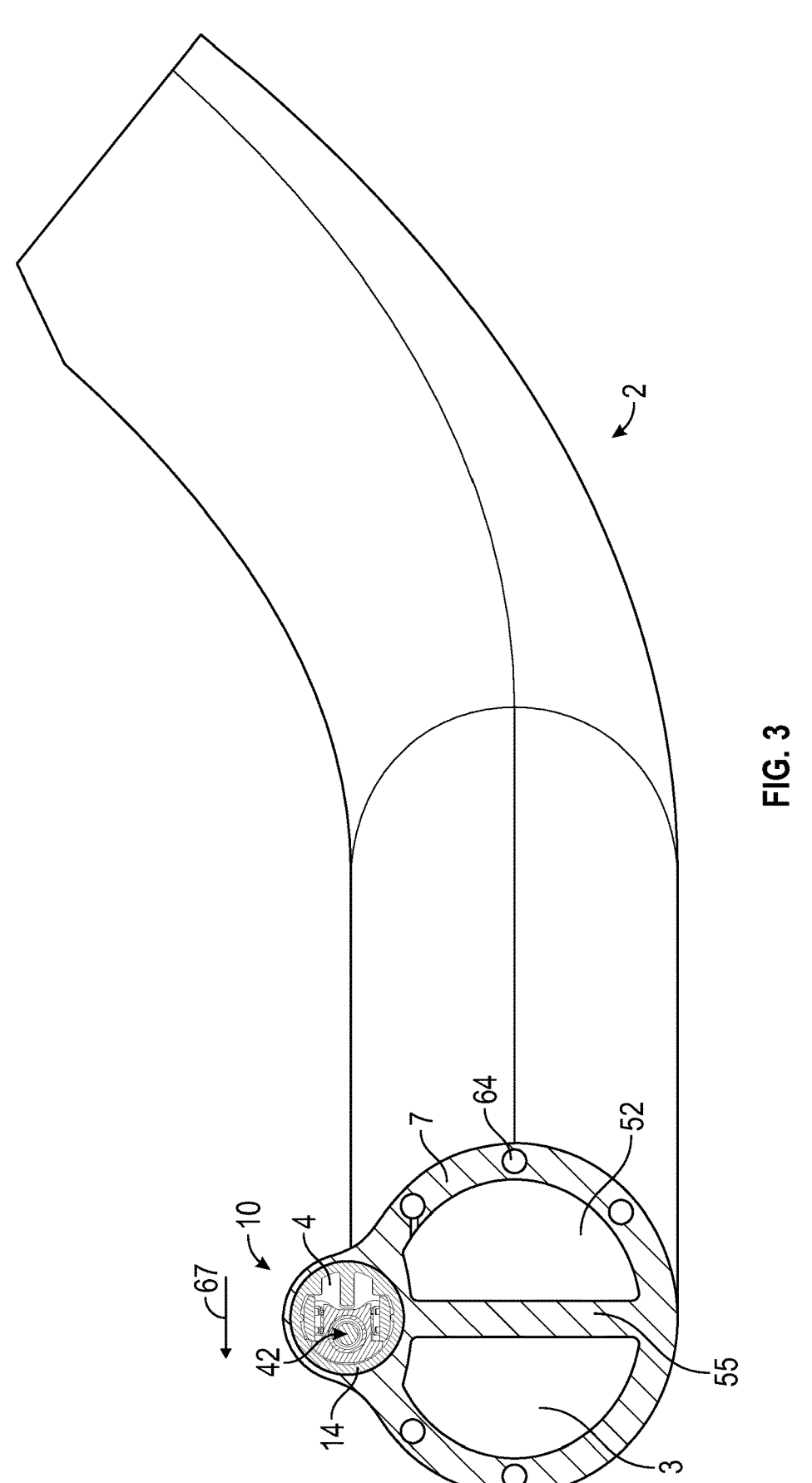
FIG. 3 illustrates a cross-section through a camera housing with camera module of the double lumen endotracheal tube of FIG. 1.

As will be described in further detail below, the endotra-cheal tube 2 furthermore includes a camera module 10 arranged in a dedicated camera lumen 4 at a distal end 9 thereof. The camera module 10 is arranged in said lumen of the tube at the distal end of the tracheal lumen 3 in order to visualise the tracheal carina and the distal end of the bronchial lumen during its insertion into the left or right bronchus. Furthermore, by means of a flush connection 62, a distal end wall 18 of a camera housing 14 including the camera module 10 may be flushed via flush openings 63 formed in the tube 2, as best seen in FIG. 2. The flush connection 62 is connected to the flush openings 63 via a number of flush channels 64 co-extruded in the outer wall 7 of tube 2 as illustrated in FIG. 3.

Figure 4:
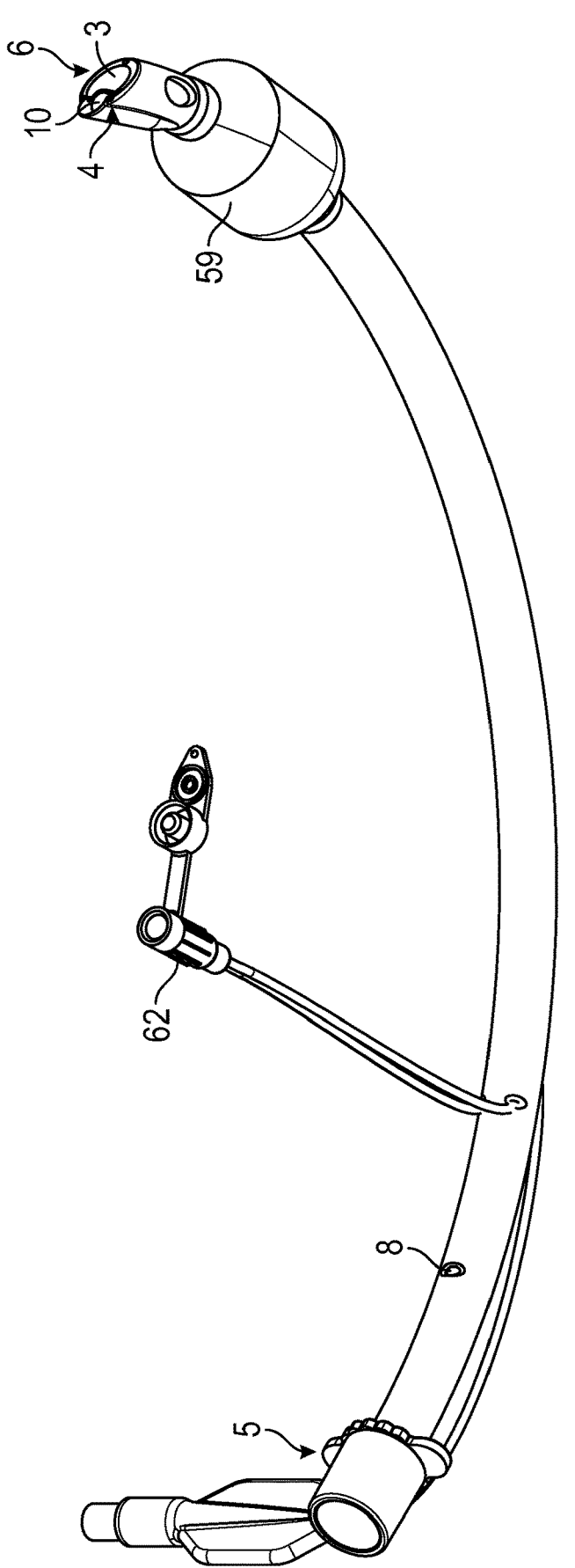
FIG. 4 is a perspective view of a single lumen endotracheal tube according to the present disclosure.

FIG. 4 illustrates another embodiment of the disclosure in the form of a single lumen endotracheal tube 2. A single lumen endotracheal tube as such is a well-known medical device and the use thereof is well-known to the skilled person. When comparing the single lumen endotracheal tube 2 of FIG. 4 with the double lumen endotracheal tube 2 of FIG. 1, it is seen that the single lumen endotracheal tube 2 of FIG. 4 does not have a second lumen 52, and therefore, the distal end 6 of the first lumen 3 also forms the distal end of the single lumen endotracheal tube 2 itself. Therefore, in the embodiment illustrated in FIG. 4, the image captured by the camera module 10 does not include any parts of the single lumen endotracheal tube 2 itself.

In the single lumen tracheal tube 2 illustrated in FIG. 4, the outer wall 7 of the tube 2 is generally ring-formed and surrounds the first lumen 3, and the camera lumen 4 is formed in the material of the outer wall 7 between an inner surface and an outer surface of the outer wall.

In a further embodiment of the medical device 1 according to the disclosure, the medical device 1 has the form of a not shown catheter of similar construction to the single lumen endotracheal tube 2 illustrated in FIG. 4. Said catheter may optionally be provided with an inflatable cuff 59 in the same way as illustrated in FIG. 4.

The present disclosure generally relates to a medical device 1 in the form of a tube 2 as illustrated in FIGS. 1 and 2. The tube has a first lumen 3 and a dedicated camera lumen 4. The first lumen 3 has a proximal end 5 and an open distal end 6, and the distal end 6 is adapted to be placed inside a body cavity during use of the medical device 1. The tube 2 has an outer wall 7 enclosing the first lumen 3 and the camera lumen 4, and the camera lumen 4 has a proximal end 8 and a distal end 9. The camera module 10 includes an image sensor 11 and one or more light sources 12 in the form of one or more LED's or incandescent bulbs. Furthermore, the light sources may be provided in the form of one or more fibre optic cables transmitting light from outside the camera module 10 to the camera module 10. The camera module 10 is arranged in the camera lumen 4 at the distal end 9 thereof so that the camera module 10 is positioned adjacent the distal end 6 of the first lumen 3. An image transmission cable 13 is attached to the camera module 10 and extends through part of the camera lumen 4 formed in the tube 2 in order to, during use, connect to a monitor or image display device 68. The camera module 10 is fixed in the camera lumen 4 by means of a camera housing 14 extending in a longitudinal direction and having a proximal end 15 and a distal end 16. The camera housing 14 includes a tubular housing part 17 surrounding the camera module 10 and a distal end wall 18.

The tubular housing part 17 is seen in FIGS. 5 to 11. The tubular housing part 17 and the distal end wall 18 are integrally moulded and form one single housing element 19. The tubular housing part 17 fits tightly into the camera lumen 4 of the tube 2. Thereby, precise mounting of the camera module 10 in the camera lumen 4 may be facilitated in that the tight fit between the tubular housing part 17 and the camera lumen 4 may ensure precise positioning of the camera module 10 in the lumen 4 without any adjustments being necessary. In particular, dilatation of the camera lumen 4 in order to mount the camera module 10 in the camera lumen may not be necessary. Thereby, production may be made easier and faster with less individual steps. Although it may be preferred that the tubular housing part 17 has a circular cross-section as illustrated in the figures, any tubular form is possible. For instance, the cross-section of the tubular housing part 17 may have any suitable rounded form, such as oval or elliptic. The cross-section of the tubular housing part 17 may also have other forms, such as a polygonal form, e.g. a triangular, square, pentagonal, hexagonal, heptagonal, octagonal form or any other suitable form.

Figure 5:
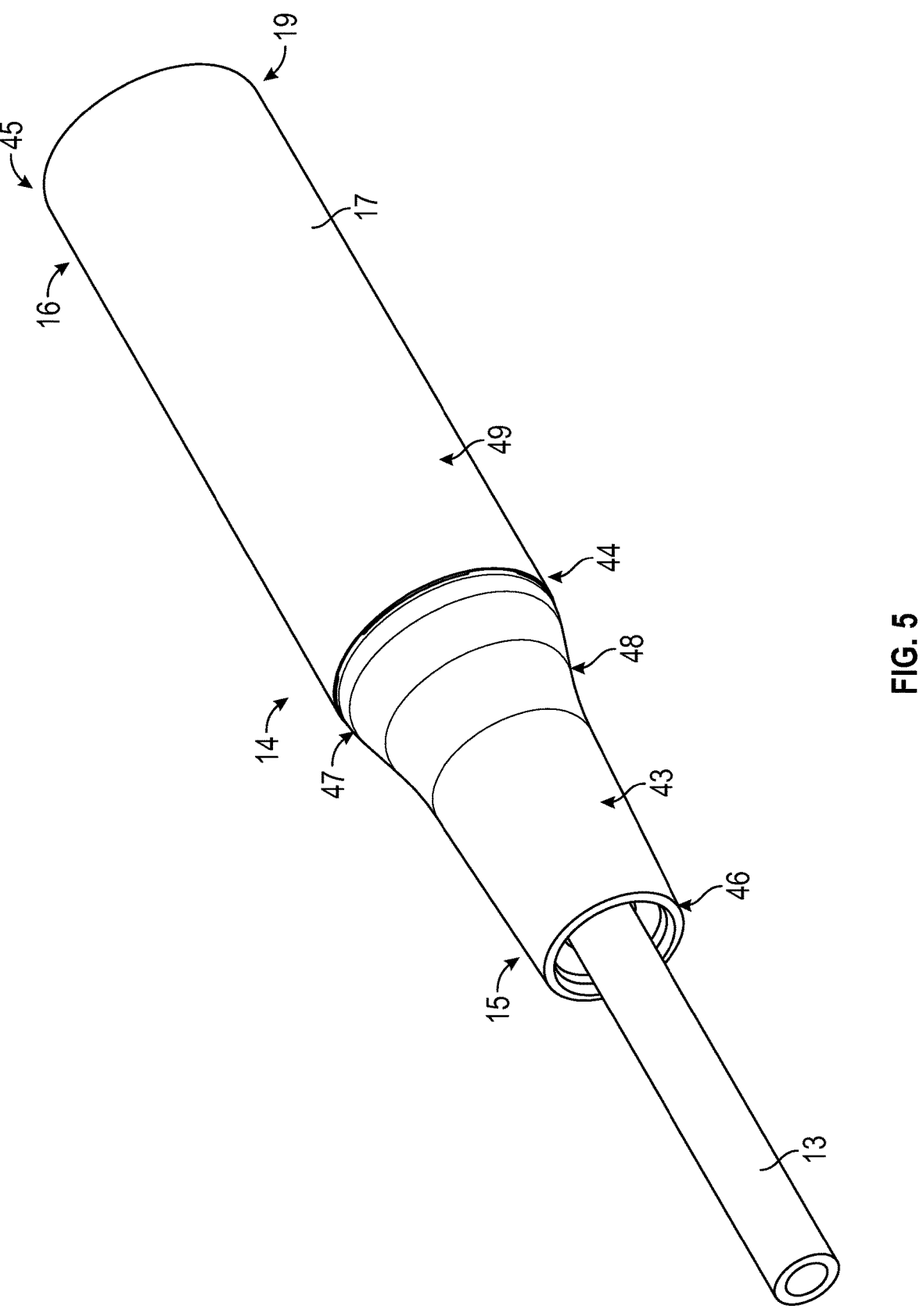
FIG. 5 is a perspective view of an assembled camera housing according to the present disclosure.

As seen in FIG. 5, the camera housing 14 includes a proximal portion 43 arranged at a proximal end 44 of the tubular housing part 17. The proximal portion 43 has a proximal end 46 and a distal end 47 and a tapering part 48 arranged between the proximal end 46 and the distal end 47. The tapering part 48 may for instance be conical. In the illustrated embodiment, the tapering part 48 is composed of a number of sections having varying configuration. An outer diameter of the proximal end 46 is smaller than an outer diameter of the distal end 47. Furthermore, the tubular housing part 17 has an outer cylindrical surface 49, and the outer diameter of the distal end 47 of the proximal portion 43 corresponds to an outer diameter of the outer cylindrical surface 49. Thereby, a smooth transition between the proximal portion 43 and the tubular housing part 17 may be ensured. The tapered part of the proximal portion 43 may make it much easier to push the camera housing into the camera lumen of the tube which may be made of a soft/flexible polymer material. Thereby, dilatation of the camera lumen 4 of the tube in order to mount the camera module 10 in the camera lumen may be even less necessary. It is noted that the outer surface of the tubular housing part 17 itself may also taper or may be slightly conical in order to facilitate insertion of the camera housing into the camera lumen of the tube 2.

Figure 19:
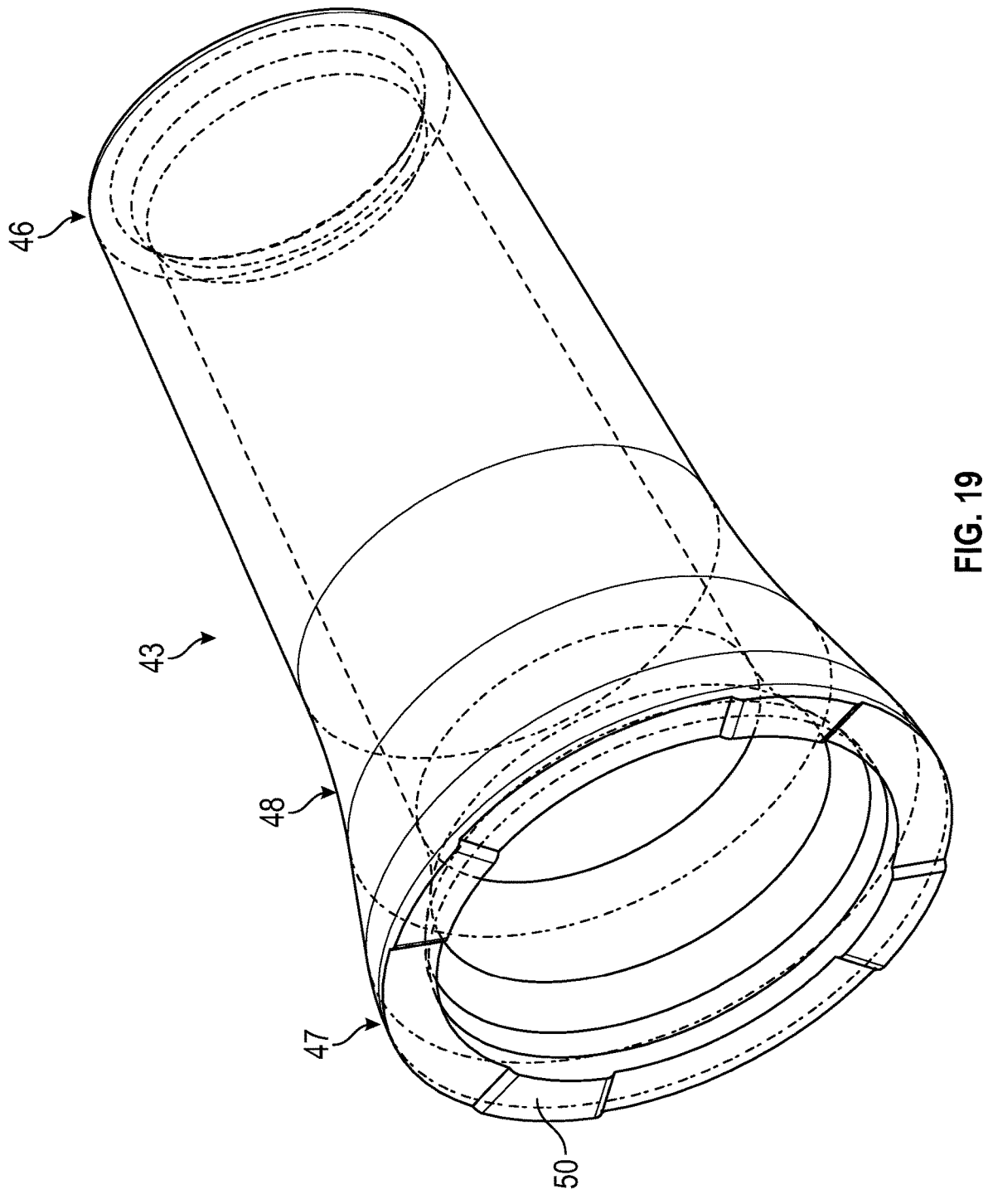
FIG. 19 illustrates a perspective view of a proximal portion of the camera housing illustrated in FIG. 5.

The proximal portion 43 is formed as a separate element attached to the tubular housing part 17, usually by means of glue. As seen in FIG. 19, the distal end 47 of the proximal portion 43 may have a number of protrusions 50 distributed in its circumferential direction and adapted to abut the proximal end 44 of the tubular part 17.

As illustrated in FIGS. 6 to 10, the camera housing 14 includes a support structure 20 for the camera module 10. The support structure 20 has a proximal end 21 and a distal end 22, and the proximal end 21 of the support structure 20 has a tubular end part 23 arranged inside the tubular housing part 17 of the camera housing 14. The image transmission cable 13 extends through the tubular end part 23 of the support structure 20, and the distal end 22 of the support structure is engaged with the camera module. Thereby, precise mounting of the camera module 10 in the camera lumen 4 may be further facilitated.

Figure 10:
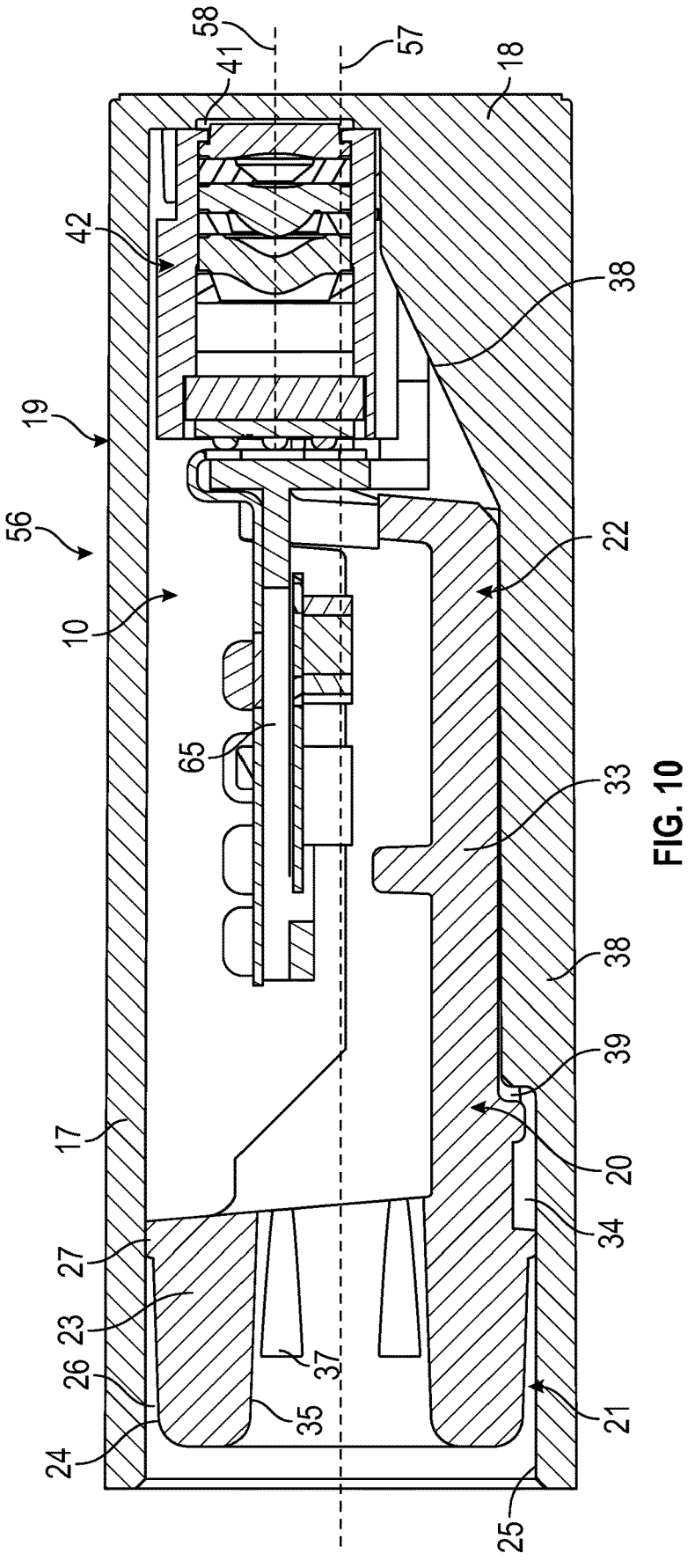
FIG. 10 is an axial section through the assembled camera housing of FIG. 5, however without the image transmission cable and the tapering proximal part.
Figure 11:
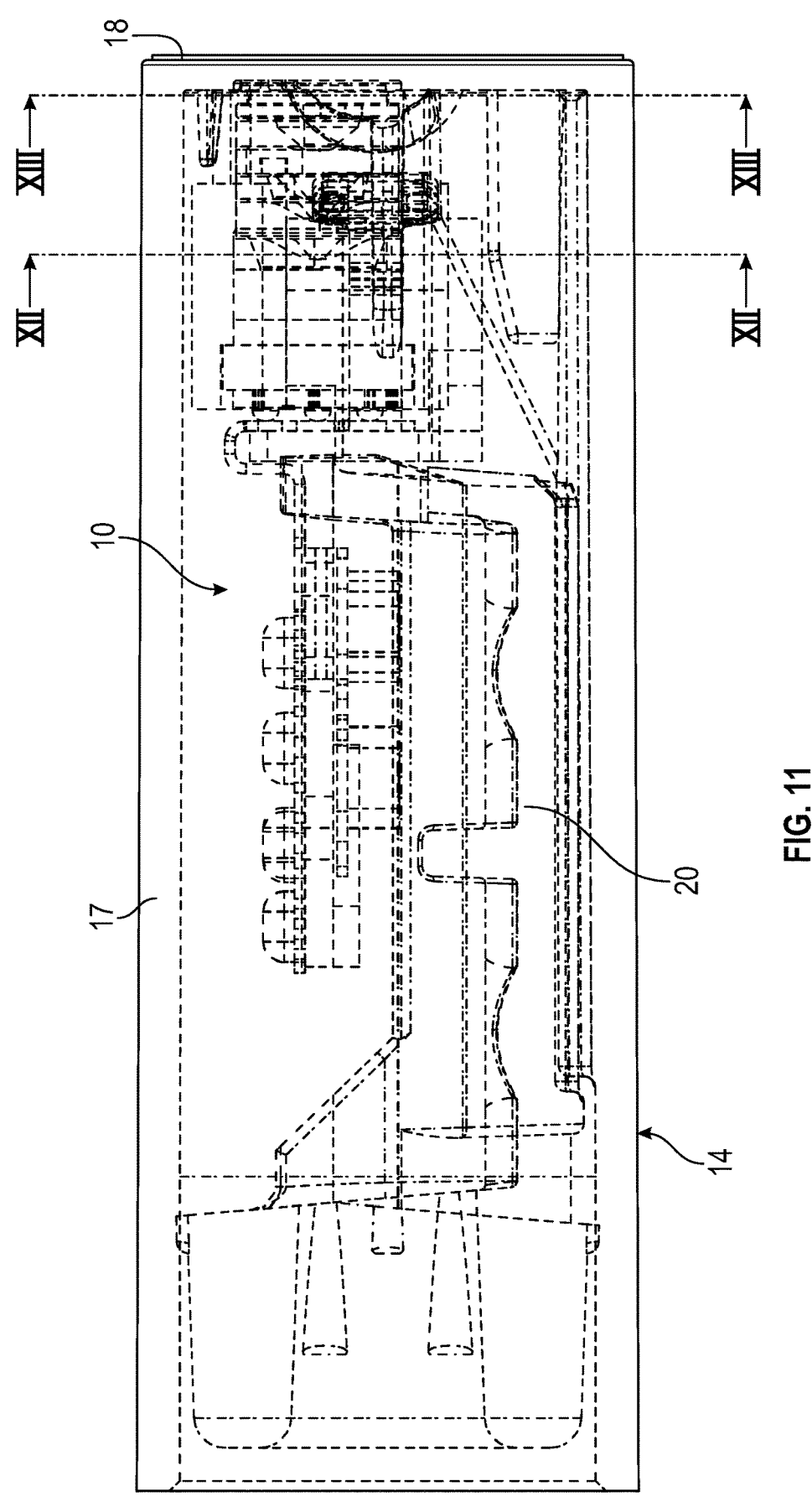
FIG. 11 is a side view of the assembled camera housing of FIG. 5, however without the image transmission cable and the tapering proximal part, with indications of sectional views.
Figure 12:
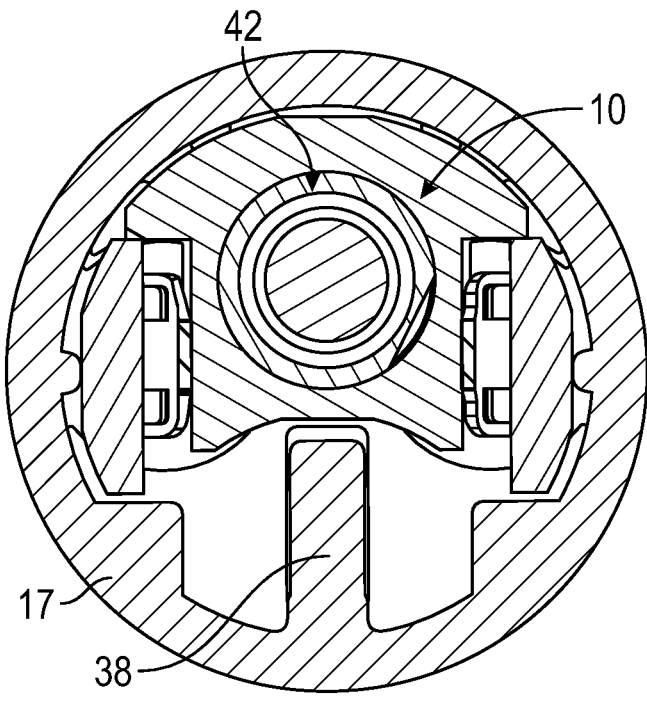
FIG. 12 is a cross-sectional view though the assembled camera housing along the line XII-XII of FIG. 11.

As best seen in FIG. 10, the tubular end part 23 of the support structure 20 has an outer face 24 being glued to an inner face 25 of the tubular housing part 17 of the camera housing 14. The outer face 24 of the tubular end part 23 of the support structure 20 is conical so that a gap 26 for glue is formed which has a cross-section generally decreasing in the direction from the proximal end 21 to the distal end 22 of the support structure 20. Thereby, correct application of glue may be ensured. Capillary effects may ensure that glue enters the gap 26 and the decreasing cross-section of the gap may serve to avoid that glue enters too far inside of the camera housing 14. Furthermore, the outer face 24 of the tubular end part 23 of the support structure 20 is provided with a number of ribs 27, 28 distributed in the circumferential direction of the outer face 24 in order to centre the support structure inside the camera housing such that the two parts can be glued together by utilizing capillary effects. As seen, the ribs 27, 28 only extend at a distal end 30 of the tubular end part 23 of the support structure 20 in order to facilitate entrance of glue into the gap.

Figure 14:
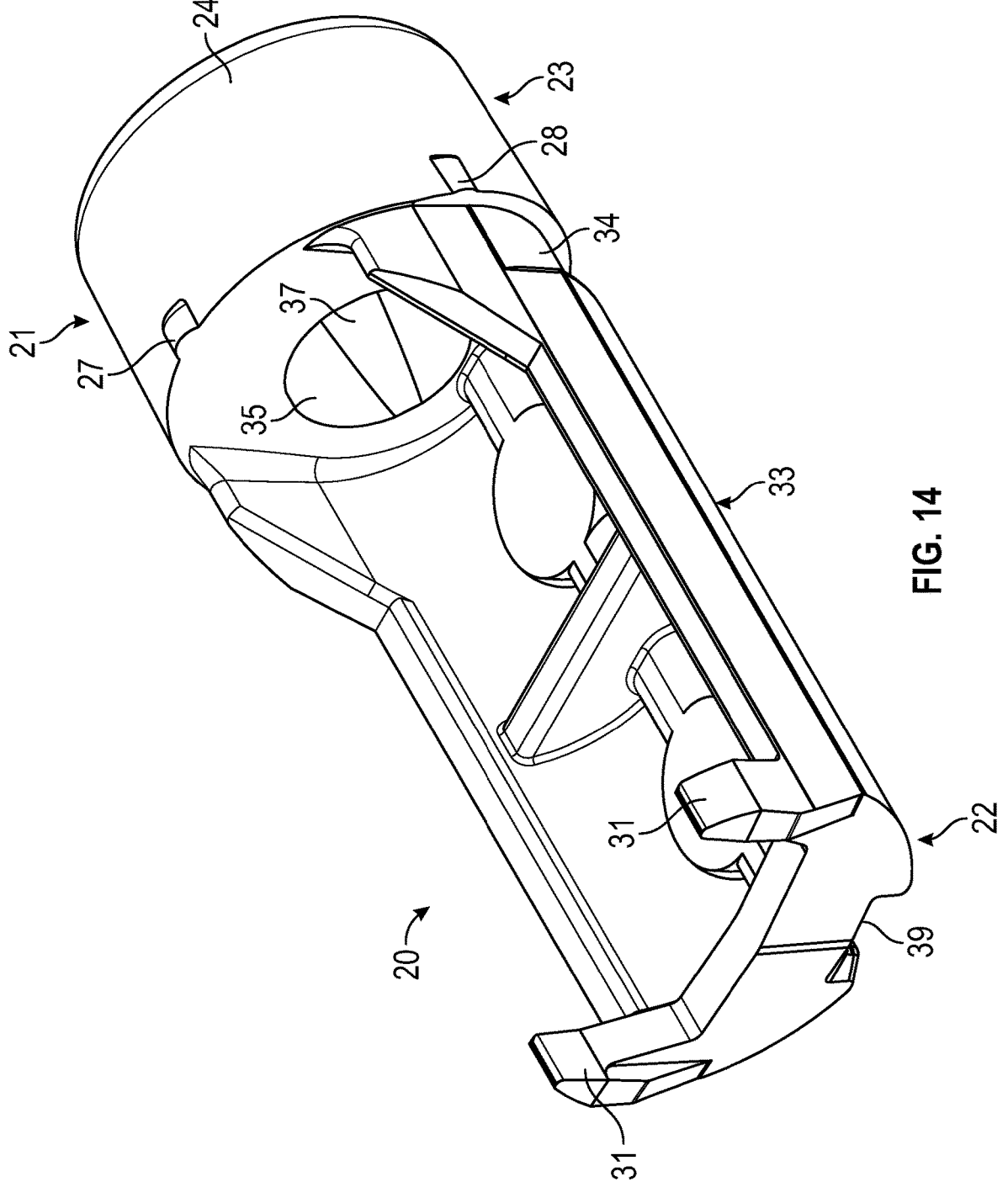
FIG. 14 is a perspective view of a support structure for the camera module according to the present disclosure.
Figure 15:
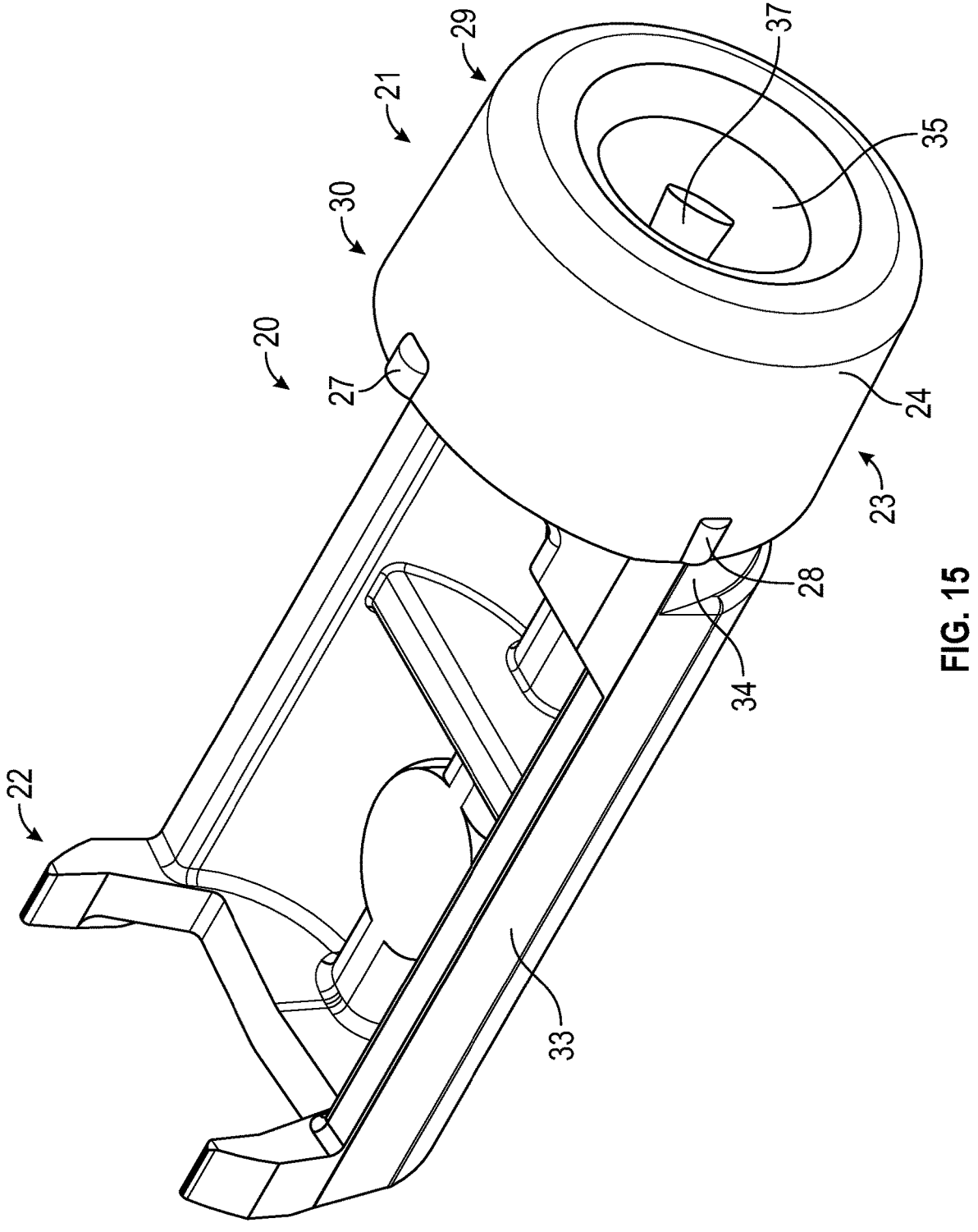
FIG. 15 is a perspective view of the support structure of FIG. 14 seen from another point of view.
Figure 16:
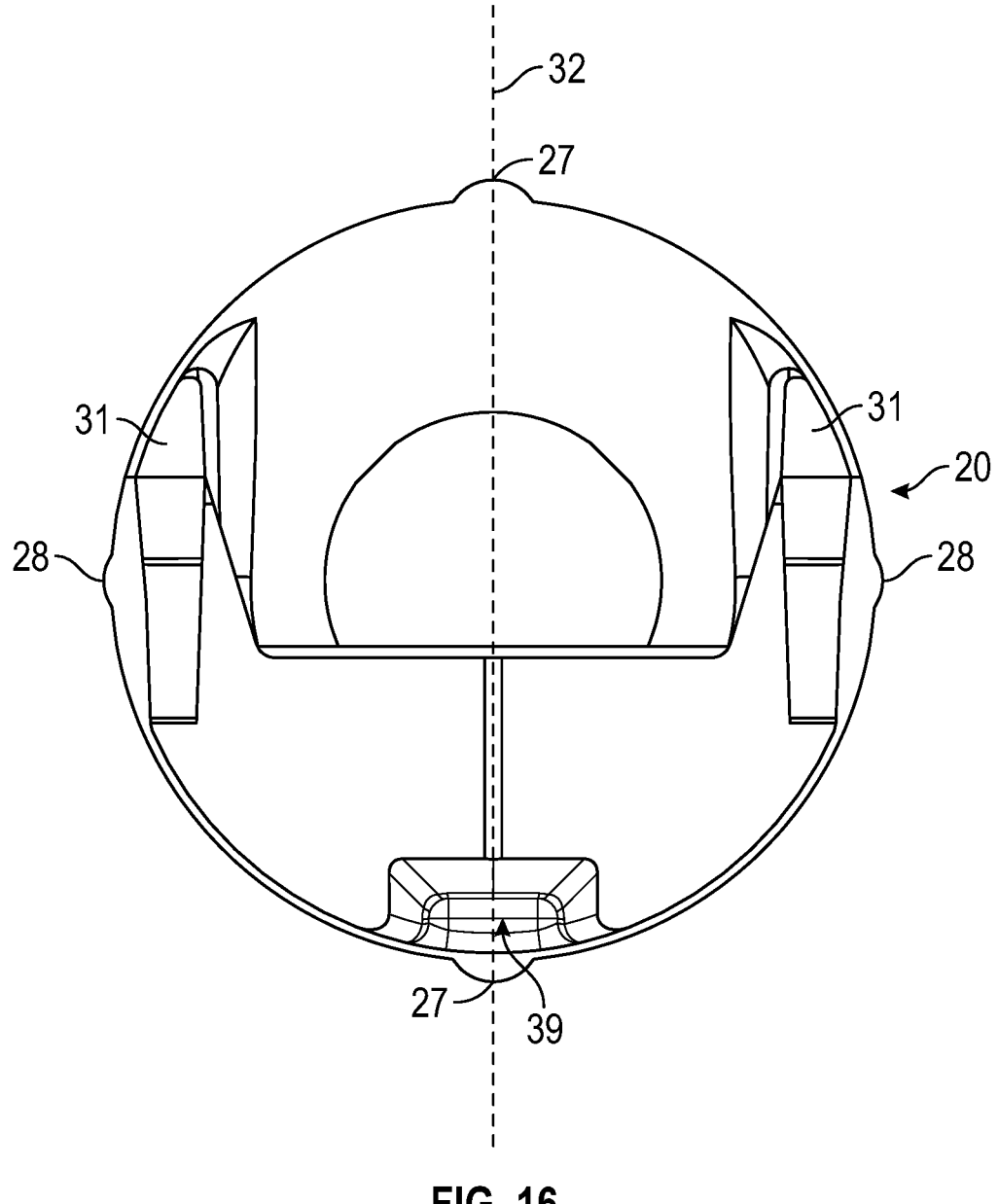
FIG. 16 is an end view of the support structure of FIG. 14 seen from a distal end thereof.

As illustrated in FIGS. 14 to 16, said ribs 27, 28 include two pivot forming ribs 27 arranged diametrically opposite of the tubular end part 23 of the support structure 20. Together the two pivot forming ribs 27 provides a relatively tight fit with the corresponding inner face 25 of the tubular part 23 of the camera housing 14. Furthermore, said ribs 27, 28 include a number of distance ribs 28 distributed peripherally about the tubular end part 23 of the support structure 20 and together they provide a relatively loose fit with the corresponding inner face 25. As seen in FIG. 16, the two pivot forming ribs 27 protrude longer in the radial direction of the tubular end part 23 than the distance ribs 28 protrude. By this arrangement of the ribs 27, 28, it may be ensured that the support structure 20 may pivot about an axis generally extending through said pivot forming ribs 27 during the insertion of the support structure 20 into the tubular part 17 of the camera housing 14. Thereby, the distal end of the support structure 20 may better engage the camera module 10 in a flexible way so that the camera module may be guided into its correct position in the camera housing.

Figure 7:
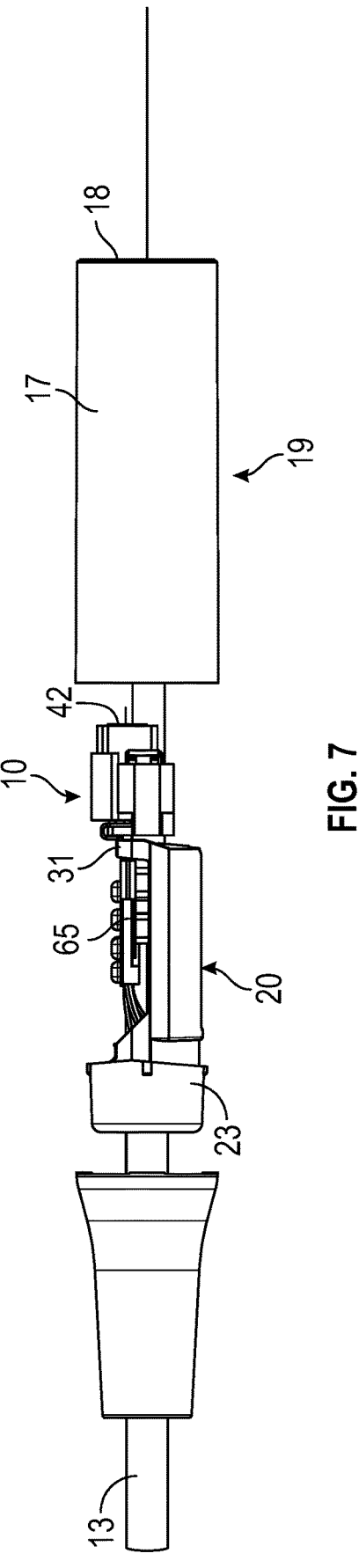
FIG. 7 is a side view of the camera housing of FIG. 5, before insertion of the camera module into the camera housing.
Figure 8:
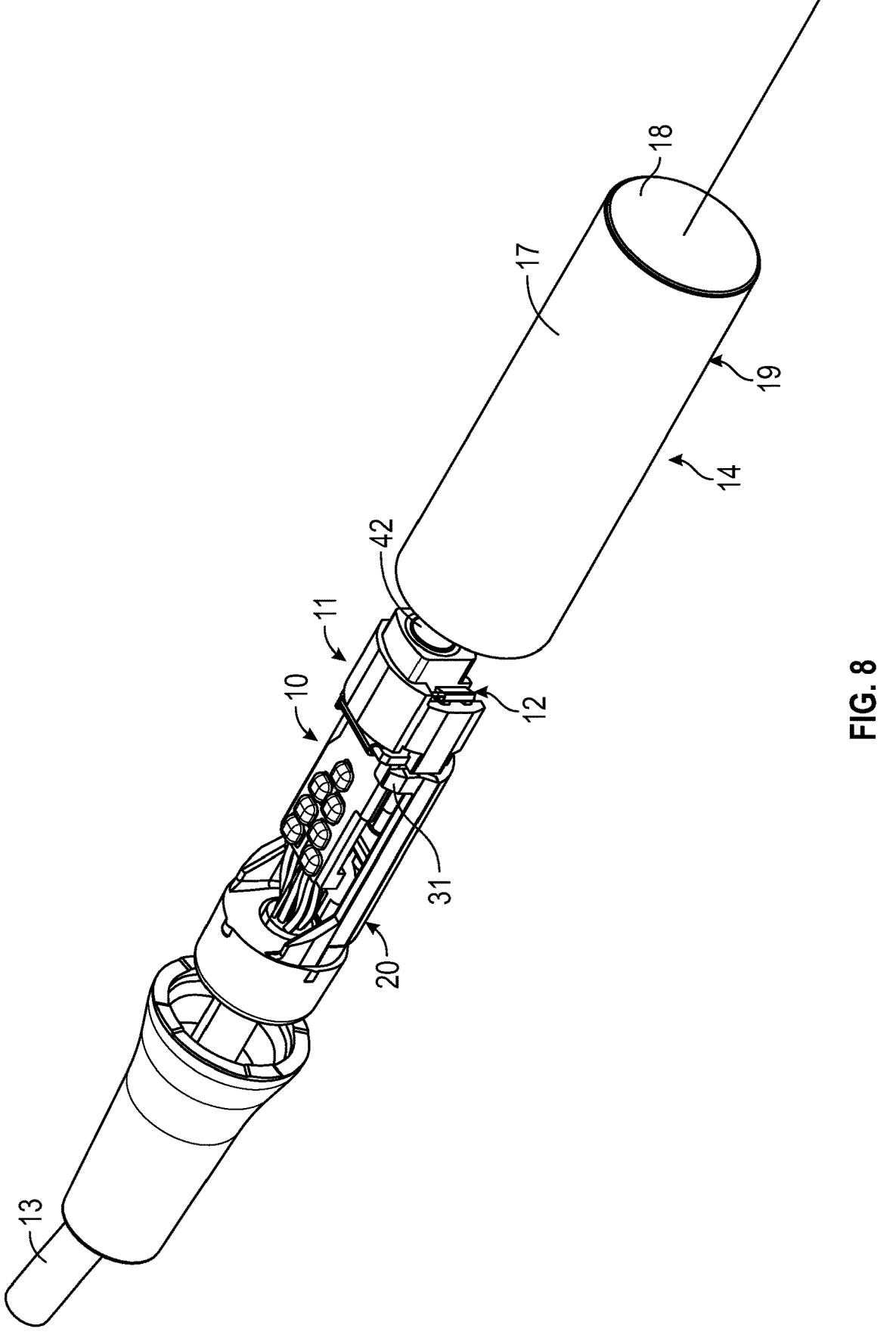
FIG. 8 is a view corresponding to that of FIG. 7, show as a perspective view.
Figure 9:
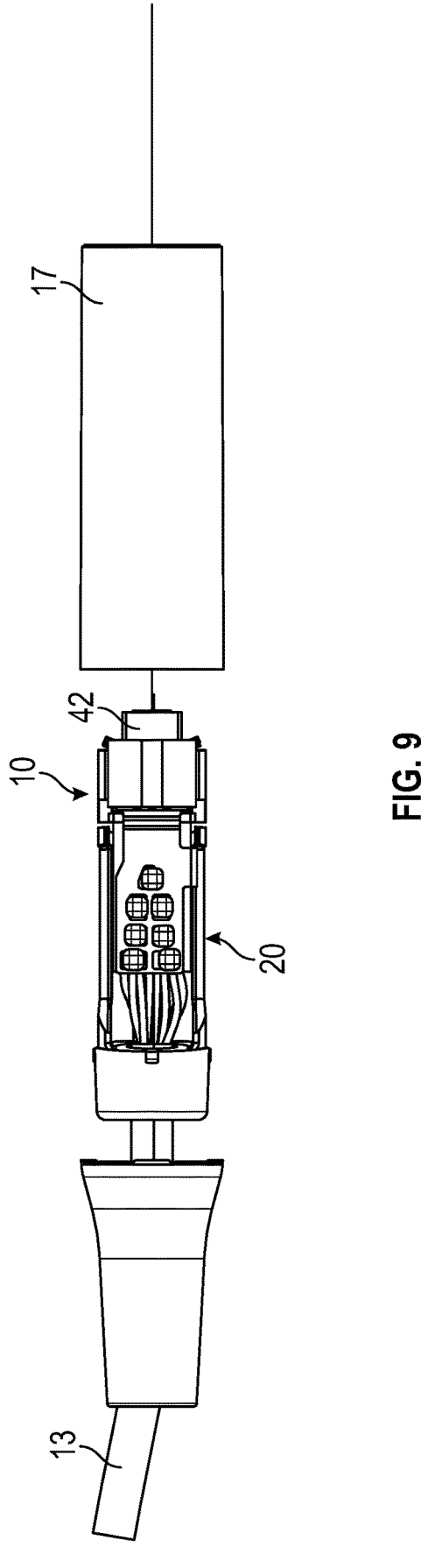
FIG. 9 is a view corresponding to that of FIG. 7, show as a top view.

Comparing FIGS. 14 and 16, it is seen that the distal end 22 of the support structure 20 is provided with two spaced tabs 31 arranged generally symmetrically about a plane 32 extending through said two pivot forming ribs 27, and the two spaced tabs 31 are adapted to abut the camera module 10 as seen in FIG. 7. Thereby, both spaced tabs 31 may tend to engage the camera module 10 during its insertion into the camera housing, thereby even better ensuring that the camera module may be guided into its correct position.

As seen in FIGS. 14 and 15, the support structure 20 includes an elongated part 33 having generally semi-circular cross-section, and the elongated part 33 connects the proximal end 21 of the support structure 20 with the two spaced tabs 31. The elongated part 33 is provided with a peripherally extending recess 34 facing the inner face 25 of the tubular part 17 of the camera housing 14 next to the tubular end part 23 of the support structure 20 in order to stop the glue from moving further into the camera housing during application.

The tubular end part 23 of the support structure 20 has an inner face 35 being glued to an outer face 36 of the image transmission cable 13. The image transmission cable 13 transmits the image data from the image sensor 11 of the camera module 10, but furthermore, the image transmission cable 13 may transmit electric energy to an electric circuit of the camera module 10 and the light source 12 of the camera module 10. Furthermore, the image transmission cable 13 may include one or more fibre optic cables transmitting light from outside the camera module 10 to the camera module 10. The inner face 35 of the tubular end part 23 of the support structure 20 is conical so that a gap for glue is formed which has a cross-section generally decreasing in the direction from the proximal end 21 to the distal end 22 of the support structure 20 in order to ensure correct application of glue. Capillary effects may ensure that glue enters the gap and the decreasing cross-section of the gap may serve to avoid that glue enters too far inside of the camera housing. In the illustrated embodiment, the inner face 35 of the tubular end part 23 of the support structure 20 is further provided with a number of ribs 37 distributed in the circumferential direction of the inner face 35 in order to ensure that image transmission cable is centred inside the tubular end part of the support structure.

Figure 17:
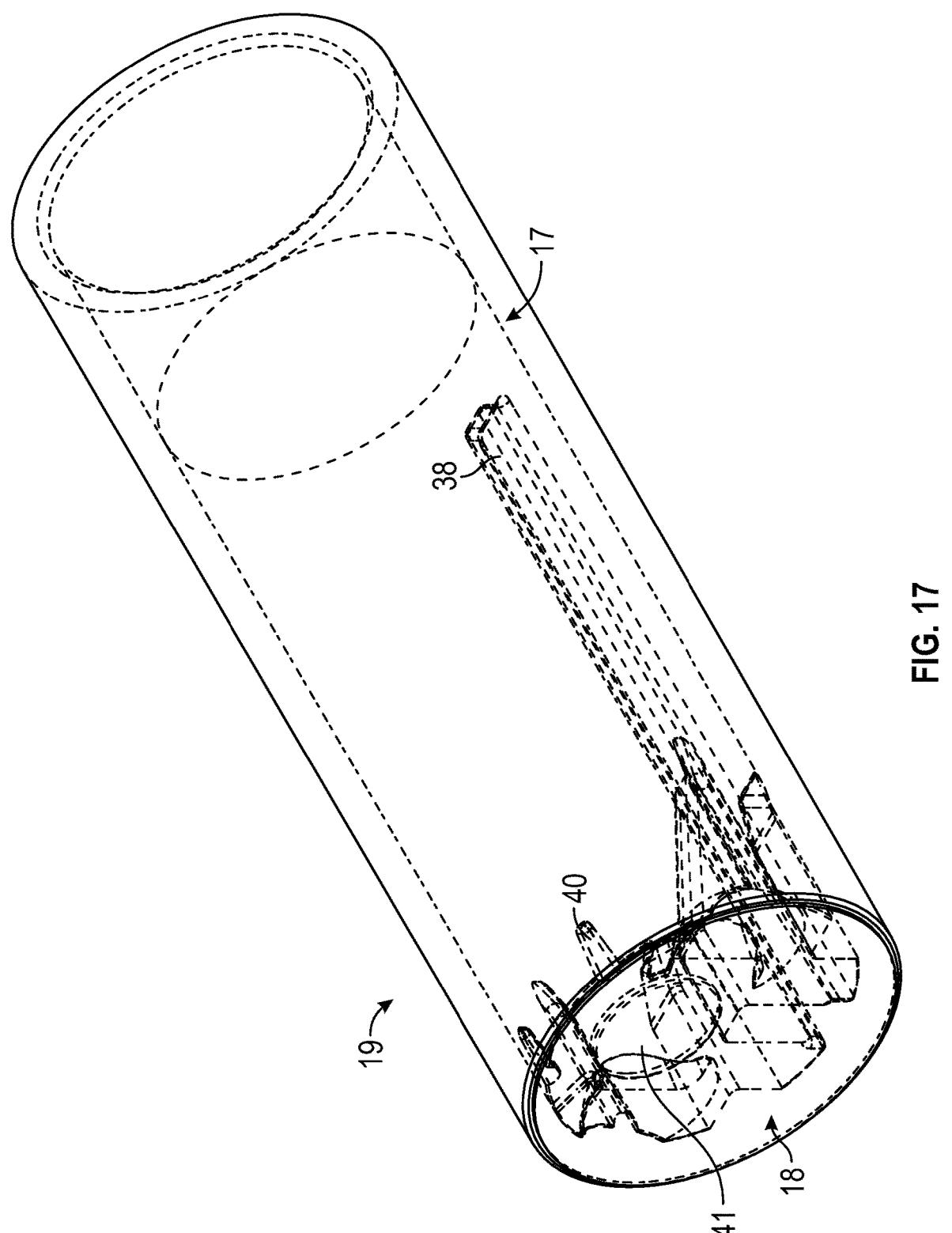
FIG. 17 is a perspective view of the camera housing of FIG. 5 without internal components inserted, but with internal features illustrated by means of broken lines.

Comparing FIGS. 14 and 17, it is seen that the inner face 35 of the tubular part 17 of the camera housing 14 has a guide rib 38 extending in the longitudinal direction of the camera housing 14, and the support structure 20 has a longitudinal groove 39, wherein the guide rib 38 is adapted to slide in the groove 39 in order to ensure that the camera module 10 is guided to the correct rotational orientation inside the camera housing 14. As seen in FIG. 16, the groove 39 is arranged symmetrically about the plane 32 extending through said two pivot forming ribs 27, and the guide rib 38 has a loose fit in the groove 39 in order to better ensure that the support structure 20 may pivot about an axis generally extending through said pivot forming ribs 27 during the insertion of the support structure into the tubular part of the camera housing. Thereby, the distal end of the support structure may better engage the camera module 10 in a flexible way so that the camera module may be guided into its correct position in the camera housing.

As seen in FIGS. 10 to 13, the camera module 10 is arranged extending from the distal end 22 of the support structure 20. The inner face 25 of the tubular part 17 of the camera housing 14 is provided with the guide rib 38, and the guide rib 38 is wedge-formed at the distal end 16 of the camera housing 14 in order to guide the camera module 10 into its correct position during the last part of the insertion procedure.

Figure 13:
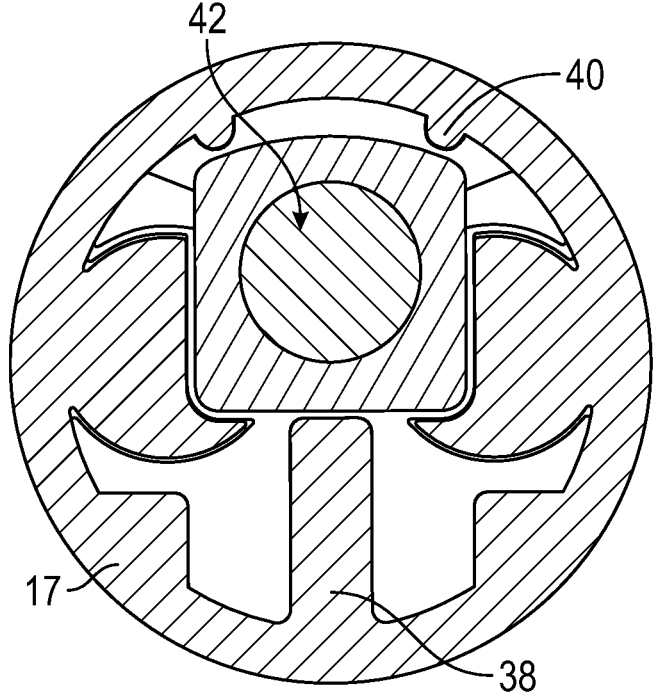
FIG. 13 is a cross-sectional view though the assembled camera housing along the line XIII-XIII of FIG. 11.
Figure 18:
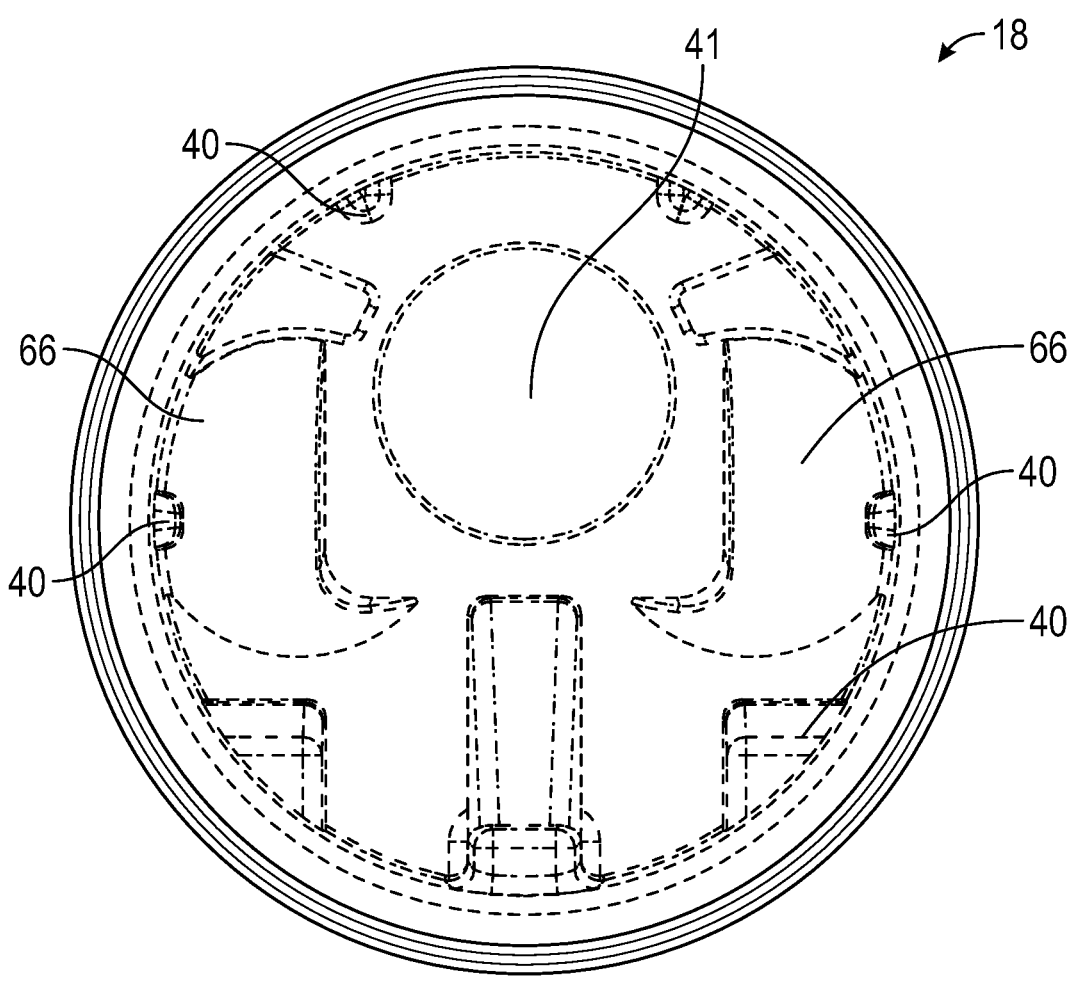
FIG. 18 is an end view of a distal end wall of the camera housing, seen from a distal end thereof, and with internal features illustrated by means of broken lines.

As illustrated in FIGS. 13 and 18, a number of guide tabs 140 are distributed in the circumferential direction of the inner face 25 of the tubular part 17 of the camera housing 14 at the distal end wall 18 of the camera housing 14. The guide tabs 40 are provided on the inner face 25 of the tubular part and on the distal end wall 18, and the guide tabs 40 are arranged to guide the camera module 10 during its insertion into the camera housing 14. As further seen in FIGS. 17 and 18, the distal end wall 18 of the camera housing 14 has a recess 41 in which at least a portion of a lens barrel 42 of the camera module 10 is inserted. At least the part of the distal end wall 18 forming the recess 41 is formed in a material which is transparent. Possibly, the transparent part of the end wall 18 may be co-moulded with material not being transparent which may form a remaining part of the end wall 18. The lens barrel 42 of the camera module 10 may for instance include a lens stack and a barrel housing carrying and/or enclosing the lens stack.

As an alternative to the recess 41, the distal end wall 18 may be provided with a through-hole wherein the lens barrel of the camera module is positioned. The camera module: would then need to be glued and sealed towards the edge of the through-hole.

Preferably, the thickness of the distal end wall 18 in the bottom of the recess 41 is less than 0.4 mm. Preferably around 0.25 mm. The thickness of the end wall 18 at the illustrated lens structures 66 is more than 1 mm. In a preferred embodiment the wall thickness of the wall of the tubular housing part 17 of camera housing is at least 0.4 mm.

Figure 6:
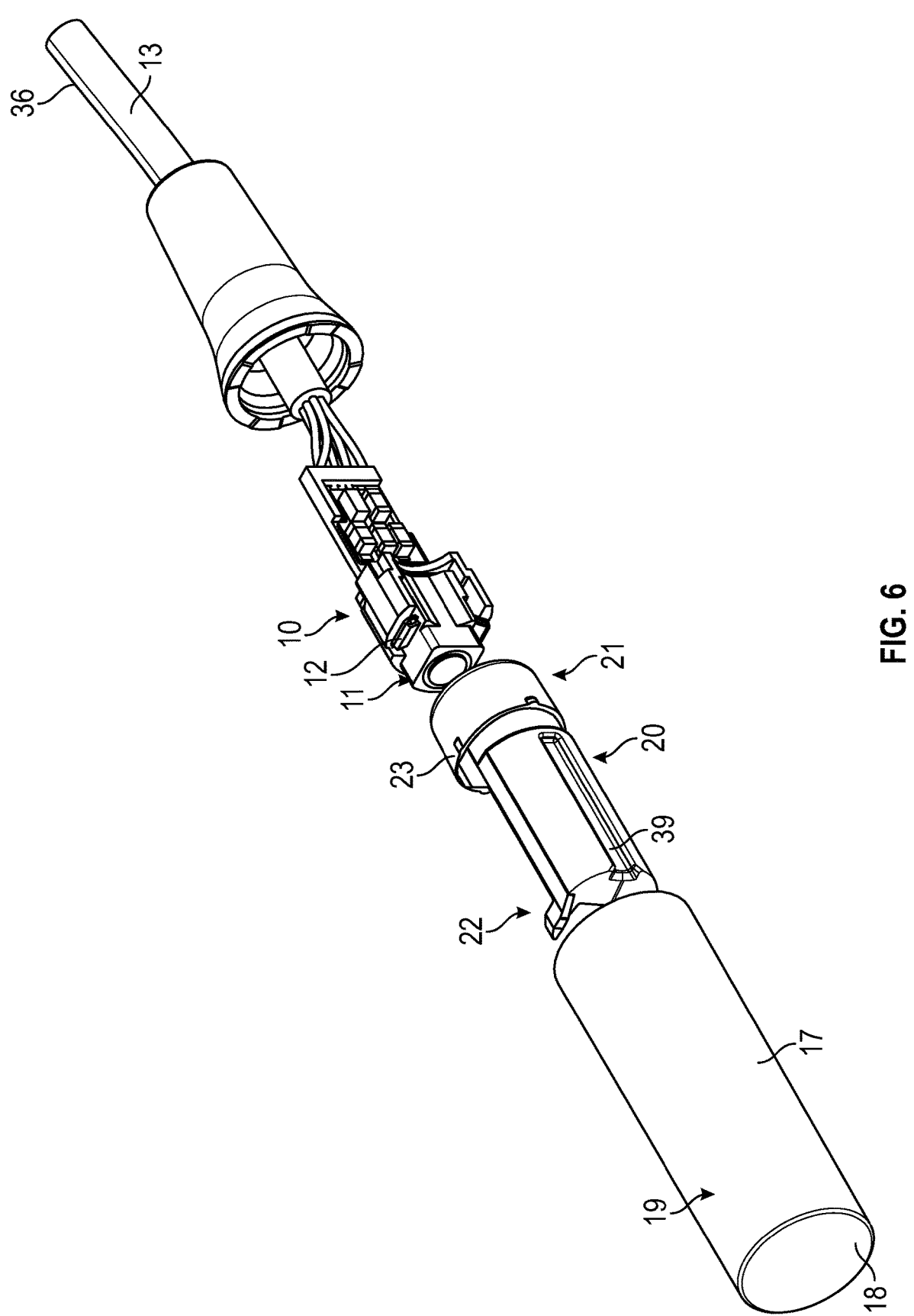
FIG. 6 is a partly exploded perspective view of the camera housing of FIG. 5.

Furthermore, as seen in FIG. 18, the distal end wall 18 of the camera housing comprises two opposed lens structures 66 which in the assembled state of the camera housing are positioned in front of the light sources 12 in the form of LEDs of the camera module 10, as seen in FIG. 6.

Figure 20:
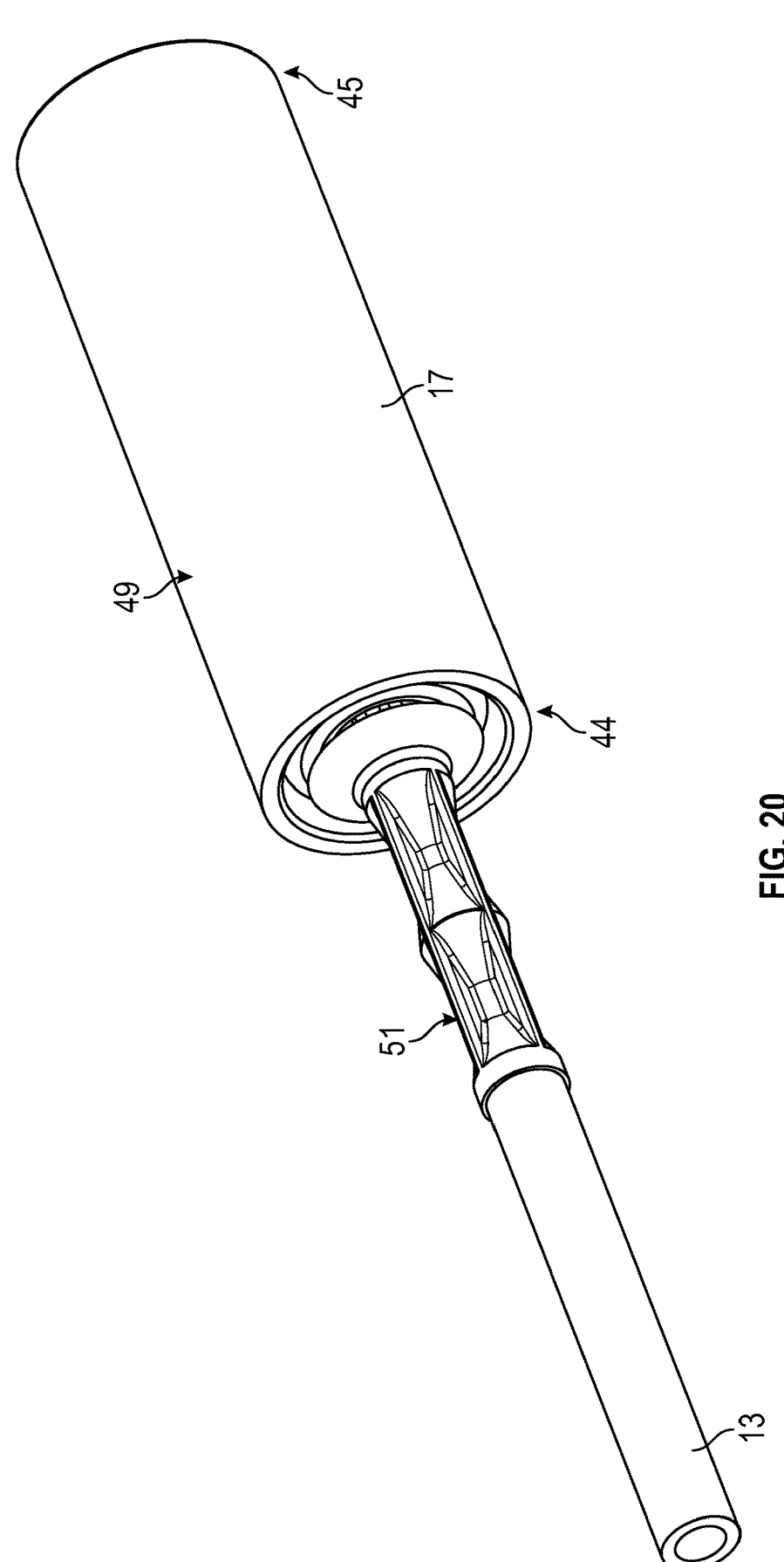
FIG. 20 is a perspective view of the camera housing corresponding to that of FIG. 5, but with the proximal portion thereof removed.
Figure 21:
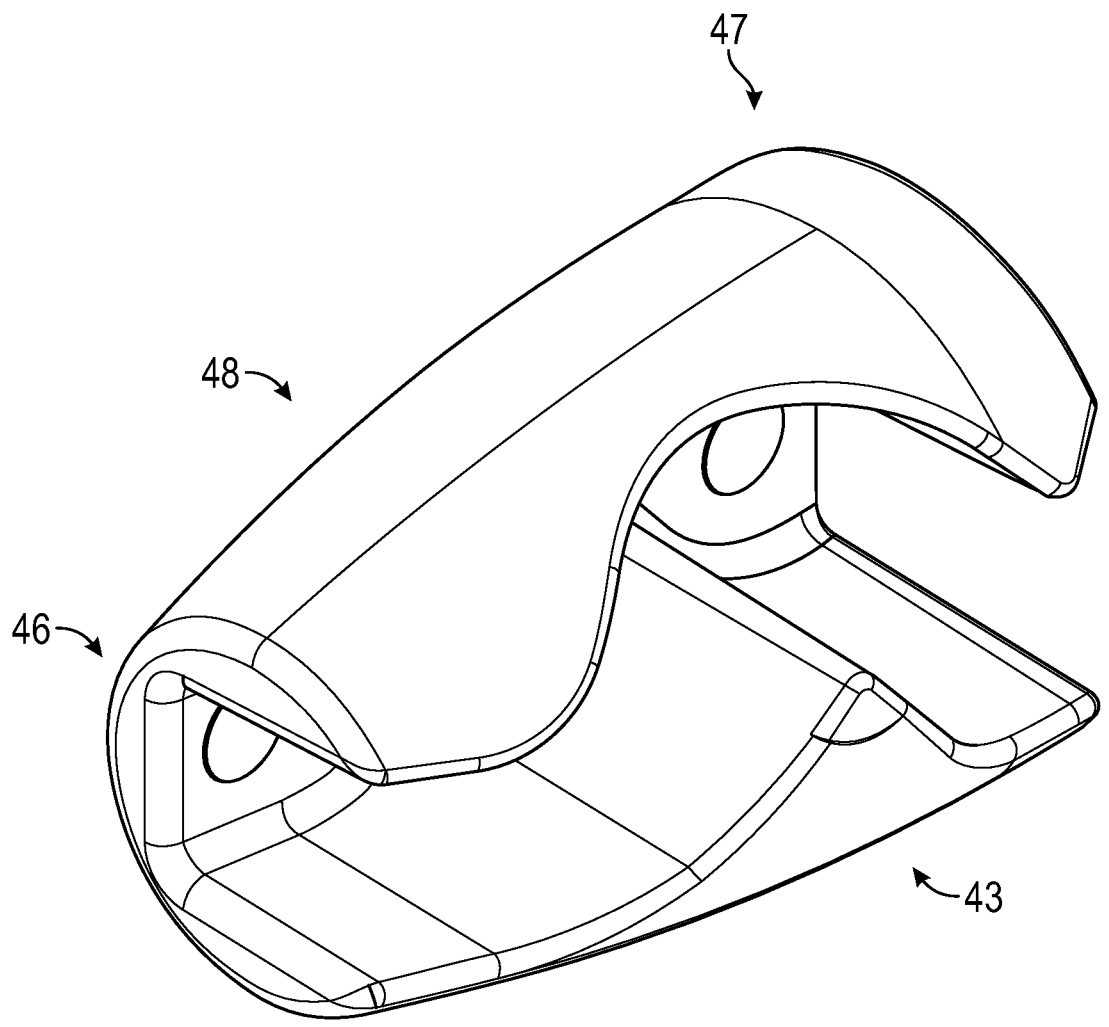
FIG. 21 illustrates a perspective view of an alternative proximal portion of the camera housing according to the present disclosure.

As illustrated in FIG. 20, the image transmission cable 13| is retained inside of the proximal portion 43 by means of a crimp 51 fixed on the image transmission cable 13 inside the proximal portion 43. Alternatively, a knot is tied on the image transmission cable 13, which is fixed inside the proximal portion 43. FIG. 21 illustrates an alternative embodiment, in which the image transmission cable 13 may be retained inside of the proximal portion 43 by means of a labyrinth in which the image transmission cable 13 may be trapped and/or glued.

As seen in FIG. 3, the outer wall 7 of the tube 2 is generally ring-formed and surrounds the first lumen 3 and the second lumen 52, and the camera lumen 4 is formed in the material of the outer wall 7 between an inner surface and an outer surface of the outer wall. As seen, the camera lumen 4 has a substantially smaller cross-section than the first lumen 3 and the second lumen 52. For instance, when the camera housing 14 is inserted into the camera lumen 4, the camera lumen 4 may at that position have a cross-sectional area being less than ½ or less than ⅓ of a cross-sectional area of the first lumen 3 or of the second lumen 52. The first lumen 3 and the second lumen 52 are separated by means of a partition wall 55 in the dual lumen tracheal tube illustrated in FIGS. 1 and 2. As further seen, the camera lumen 4 is formed in the material of the outer wall 7 at a position where the partition wall 55 is connected to the outer wall 7. As also seen, the first lumen 3 and the second lumen 52 are generally symmetrically arranged about the partition wall 55 and in relation to the camera lumen 4.

As illustrated in FIG. 10, the tubular housing part 17 of the camera housing 14 has a cylindrical outer surface 56 having a central axis 57 of symmetry, and a lens barrel 42 of the camera module 10 is eccentrically arranged in relation to the cylindrical outer surface of the tubular housing part. When further comparing with FIG. 3, it is understood that a central axis 58 of the lens barrel 42 of the camera module is displaced in relation to the central axis 57 of symmetry of the cylindrical outer surface 56 of the tubular housing part 17 of the camera housing 14 in a direction 67 so that the lens barrel 42 is closer to the first lumen 3 than to the second lumen 52. Thereby, it may be ensured that the viewing angle of the camera module 10 covers relatively more of the surroundings of the tube 2 than it covers of the part of the tube enclosing the second lumen 52 distally of the first lumen 3. Thereby, it may be ensured that the image captured by the camera module 10 shows more of the anatomy and less of the tubing of the second bronchial lumen 52 provided with the second inflatable cuff 60 which is inserted into the bronchus.

The following items correspond to the original claims.

1. A medical device including a tube having at least a first lumen and a dedicated camera lumen, the first lumen having a proximal end and an open distal end, the distal end being adapted to be placed inside a body cavity during use of the medical device, the tube having an outer wall enclosing at least the first lumen and the camera lumen, the camera lumen having a proximal end and a distal end, a camera module including at least an image sensor and one or more light sources being arranged in the camera lumen at the distal end thereof so that the camera module is positioned adjacent the distal end of the first lumen, and an image transmission cable attached to the camera module extending through at least part of the camera lumen in order to connect to an image display device, wherein the camera module is fixed in the camera lumen by means of a camera housing extending in a longitudinal direction and having a proximal end and a distal end, wherein the camera housing includes a tubular housing part at least partly surrounding the camera module and a distal end wall, wherein the tubular housing part and the distal end wall are integrally moulded and form one single housing element, and wherein the tubular housing part fits tightly into the camera lumen of the tube.

2. A medical device according to item 1, wherein the camera housing includes a support structure for the camera module, wherein the support structure has a proximal end and a distal end, wherein the proximal end of the support structure has a tubular end part arranged inside the tubular housing part of the camera housing, wherein the image transmission cable extends through the tubular end part of the support structure, and wherein the distal end of the support structure is engaged with the camera module.

3. A medical device according to item 2, wherein the tubular end part of the support structure has an outer face being glued to an inner face of the tubular part of the camera housing.

4. A medical device according to item 3, wherein the outer face of the tubular end part of the support structure and/or the inner face of the tubular housing part of the camera housing are/is tapered or conical so that a gap for glue is formed, a cross-section of said gap generally decreasing in the direction from the proximal end to the distal end of the support structure.

5. A medical device according to item 3 or 4, wherein the outer face of the tubular end part of the support structure and/or the inner face of the tubular housing part of the camera housing are/is provided with a number of ribs distributed in the circumferential direction of the outer face and/or the inner face.

6. A medical device according to item 5, wherein the ribs only extend at a distal end of the tubular end part of the support structure.

7. A medical device according to item 5 or 6, wherein said ribs include two pivot forming ribs arranged diametrically opposite of the tubular end part of the support structure and/or of the tubular part of the camera housing and together providing a relatively tight fit with the corresponding outer face or inner face, wherein said ribs further include at least two distance ribs distributed peripherally about the tubular end part of the support structure and/or of the tubular part of the camera housing and together providing a relatively loose fit with the corresponding outer face or inner face, and wherein, preferably, the two pivot forming ribs protrude longer in the radial direction of the tubular end part than the distance ribs protrude.

8. A medical device according to item 7, wherein the distal end of the support structure is provided with two spaced tabs arranged generally symmetrically about a plane extending through said two pivot forming ribs, and wherein the two spaced tabs are adapted to abut the camera module.

9. A medical device according to item 8, wherein the support structure includes an elongated part having generally semi-circular cross-section, and wherein the elongated part connects the proximal end of the support structure with the two spaced tabs.

10. A medical device according to item 9, wherein the elongated part is provided with a peripherally extending recess facing the inner face of the tubular part of the camera housing next to the tubular end part of the support structure.

11. A medical device according to any one of the items 2 to 10, wherein the tubular end part of the support structure has an inner face being glued to an outer face of the image transmission cable.

12. A medical device according to item 11, wherein the inner face of the tubular end part of the support structure is tapered or conical so that a gap for glue is formed, a cross-section of said gap generally decreasing in the direction from the proximal end to the distal end of the support structure.

13. A medical device according to item 11 or 12, wherein the inner face of the tubular end part of the support structure is provided with a number of ribs distributed in the circumferential direction of the inner face.

14. A medical device according to any one of the items 2 to 13, wherein the support structure or the inner face of the tubular part of the camera housing has a guide rib ex-tending in the longitudinal direction of the camera housing, wherein the corresponding one of the support structure and the inner face of the tubular part of the camera housing has a groove extending in the longitudinal direction of the camera housing, and wherein the guide rib is adapted to slide in the groove.

15. A medical device according to item 14, wherein the camera module is arranged ex-tending from the distal end of the support structure, wherein the inner face of the tubular part of the camera housing is provided with the guide rib, and wherein the guide rib is wedge-formed at the distal end of the camera housing in order to guide the camera module.

16. A medical device according to items 9 and 14, wherein the inner face of the tubular part of the camera housing is provided with the guide rib, wherein the elongated part is provided with the groove extending in the longitudinal direction of the camera housing, wherein the groove is arranged symmetrically about the plane extending through said two pivot forming ribs, and wherein, preferably, the guide rib has a loose fit in the groove.

17. A medical device according to any one of the preceding items, wherein a number of guide tabs are distributed in the circumferential direction of the inner face of the tubular part of the camera housing at the distal end wall of the camera housing, wherein the guide tabs are provided on the inner face of the tubular part and/or on the distal end wall, and wherein the guide tabs are arranged to guide the camera module during its insertion into the camera housing.

18. A medical device according to any one of the preceding items, wherein the distal end wall of the camera housing has a recess in which at least a portion of a lens barrel of the camera module is inserted.

19. A medical device according to any one of the preceding items, wherein the camera housing includes a proximal portion arranged at a proximal end of the tubular housing part, wherein the proximal portion has a proximal end and a distal end and a tapering part arranged between the proximal end and the distal end, and wherein an outer diameter of the proximal end is smaller than an outer diameter of the distal end.

20. A medical device according to item 19, wherein the tubular housing part has an outer cylindrical surface, and wherein the outer diameter of the distal end of the proximal portion corresponds to an outer diameter of the outer cylindrical surface.

21. A medical device according to item 19 or 20, wherein the proximal portion is a separate element attached to the tubular housing part.

22. A medical device according to item 21, wherein the distal end of the proximal portion has a number of protrusions distributed in its circumferential direction and abutting the proximal end of the tubular part, and wherein the tubular part and the proximal portion are connected by means of glue.

23. A medical device according to item 21, wherein the proximal end of the tubular part has a number of protrusions distributed in its circumferential direction and abutting the distal end of the proximal portion, and wherein the tubular part and the proximal portion are connected by means of glue.

24. A medical device according to any one of the items 19 to 23, wherein the image transmission cable is retained inside of the proximal portion.

25. A medical device according to item 24, wherein a crimp is fixed on the image trans-mission cable inside the proximal portion.

26. A medical device according to any one of the preceding items, wherein the first lumen and the camera lumen, and an optional second lumen, are co-extruded to form the tube.

27. A medical device according to any one of the preceding items, wherein the outer wall of the tube is generally ring-formed and surrounds at least the first lumen, and wherein the camera lumen is formed in the material of the outer wall between an inner surface and an outer surface of the outer wall.

28. A medical device according to item 27, wherein the outer wall of the tube further surrounds at least part of a second lumen having a proximal end and an open distal end, and wherein the first lumen and the second lumen are separated by means of a partition wall.

29. A medical device according to item 28, wherein the camera lumen is formed in the material of the outer wall at a position where the partition wall is connected to the outer wall.

30. A medical device according to any one of the preceding items, wherein the outer wall of the tube surrounds the first lumen and a second lumen, wherein the first lumen and the second lumen are separated by means of a partition wall, and wherein the camera lumen is formed at the outer wall at a position where the partition wall is connected to the outer wall.

31. A medical device according to item 30, wherein the first lumen and the second lumen are symmetrically arranged about the partition wall and in relation to the camera lumen.

32. A medical device according to item 30 or 31, wherein the tubular housing part of the camera housing has a cylindrical outer surface having a central axis of symmetry, and wherein a lens barrel of the camera module is eccentrically arranged in relation to the cylindrical outer surface of the tubular housing part.

33. A medical device according to item 32, wherein a central axis of the lens barrel of the camera module is displaced in relation to the central axis of symmetry of the cylindrical outer surface of the tubular housing part of the camera housing in a direction so that the lens barrel is closer to the first lumen than to the second lumen.

34. A medical device according to any one of the preceding items, wherein the medical device is a catheter.

35. A medical device according to any one of the preceding items, wherein the medical device is an airway device.

36. A medical device according to any one of the preceding items, wherein the medical device is a double lumen endotracheal tube having a first lumen in the form of a tracheal lumen and a second lumen in the form of a bronchial lumen, wherein the first lumen and the second lumen extend together from the proximal end of the first lumen to the distal end of the first lumen, and wherein the second lumen extends further from the distal end of the first lumen to a distal end of the second lumen.

37. A medical device according to item 36, wherein the double lumen endotracheal tube has a first inflatable cuff arranged proximally the open distal end of the first lumen and a second inflatable cuff arranged proximally the open distal end of the second lumen.

38. A medical device according to any one of the items 1 to 35, wherein the medical de-vice is a single lumen endotracheal tube.

39. A medical device according to item 38, wherein the single lumen endotracheal tube has a first inflatable cuff arranged proximally the open distal end of the first lumen.

40. A system including a medical device according to any one of the preceding items, wherein the system includes a monitor or image display device connected to the image transmission cable directly or by means of a wireless connection.

LIST OF REFERENCE NUMBERS 1 medical device
2 tube
3 first lumen of tube
4 camera lumen
5 proximal end of first lumen
6 distal end of first lumen
7 outer wall of tube
8 proximal end of camera lumen
9 distal end of camera lumen
10 camera module
11 image sensor
12 light source
13 image transmission cable
14 camera housing
15 proximal end of camera housing
16 distal end of camera housing
17 tubular housing part of camera housing
18 distal end wall of camera housing
19 single housing element formed by tubular housing part and distal end wall
20 support structure
21 proximal end of support structure
22 distal end of support structure
23 tubular end part of support structure
24 outer face of tubular end part
25 inner face of tubular housing part of camera housing
26 gap for glue
27 pivot forming rib
28 distance rib
29 proximal end of tubular end part
30 distal end of tubular end part
31 tab of support structure
32 plane of symmetry of support structure
33 elongated part of support structure
34 peripherally extending recess of elongated part
35 inner face of tubular end part of support structure
36 outer face of image transmission cable
37 ribs of inner face of tubular end part of support structure
38 longitudinal guide rib of tubular part of camera housing
39 longitudinal groove of support structure
40 guide tab of camera housing
41 recess of distal end wall of camera housing
42 lens barrel of camera module
43 proximal portion of camera housing.
44 proximal end of tubular housing part
45 distal end of tubular housing part
46 proximal end of proximal portion
47 distal end of proximal portion
48 tapering part of proximal portion
49 outer cylindrical surface of tubular housing part
50 protrusion of distal end of proximal portion

17

51 crimp
52 second lumen of tube
53 proximal end of second lumen
54 distal end of second lumen.
55 partition wall
56 cylindrical outer surface of tubular housing part
57 central axis of symmetry of cylindrical outer surface
58 central axis of lens barrel
59 first inflatable cuff
60 second inflatable cuff
61 pilot balloon with one-way valve
62 flush connection
63 flush opening
64 flush channel
65 printed circuit board of camera module
66 lens structure
67 direction
68 monitor or image display device

The invention claimed is:

1. A medical device including:
    a tube having an outer wall, a first lumen and a camera lumen, the first lumen having a proximal end and a distal end, the camera lumen having a proximal end and a distal end, and the outer wall enclosing the first lumen and the camera lumen;
    a camera housing including a proximal portion and a singular housing element affixed to the proximal portion, the singular housing element comprising a tubular housing part integrally moulded in one-piece with a distal end wall, the tubular housing part sized to fit tightly into the camera lumen of the tube, the tubular housing part having an inner face, a proximal end and a distal end;
    a support structure positioned in the camera housing and comprising a proximal end, a distal end, and a tubular end part at the proximal end of the support structure, the tubular end part having an outer face forming a gap with the inner face of the tubular housing part;
    an adhesive in the gap affixing the support structure to the singular housing element; and
    a camera module supported by the support structure inside the camera housing, the camera module including an image sensor and a light source positioned at the distal end of the camera lumen adjacent the distal end of the first lumen,
    wherein the outer face of the tubular end part of the support structure and/or the inner face of the tubular housing part of the camera housing are/is tapered or conical so that the gap has a cross-section that decreases in the direction from the proximal end to the distal end of the support structure.

2. The medical device of claim 1, further comprising an image transmission cable having an outer face, wherein the inner face of the tubular end part of the support structure is adhesively bonded to the outer face of the image transmission cable.

3. The medical device of claim 1, wherein the proximal portion of the camera housing comprises a proximal end, a distal end and a tapering part between the proximal end and the distal end, and wherein an outer diameter of the proximal end is smaller than an outer diameter of the distal end.

4. The medical device of claim 1, wherein the outer wall comprises an inner surface and an outer surface, wherein the camera lumen is formed in the outer wall between the inner surface and the outer surface of the outer wall.

5. The medical device of claim 1, wherein the proximal portion of the camera housing comprises a proximal end, a distal end and a tapering part between the proximal end and the distal end, wherein an outer diameter of the proximal end is smaller than an outer diameter of the distal end, wherein the distal end comprises an end face transverse to a longitudinal axis of the camera housing and protrusions extending longitudinally from the end face.

6. The medical device of claim 1, wherein the camera assembly includes a lens barrel having a central axis, wherein the distal end wall of the singular housing element comprises a recess, wherein at least a portion of the lens barrel is positioned in the recess, and wherein the distal end of the tubular housing part comprises guide tabs configured to guide the camera module during insertion of the camera module into the singular housing element.

7. The medical device of claim 1, wherein the inner face of the singular housing element comprises a guide rib, wherein a distal end of the guide rib is wedge-formed, wherein the support structure comprises an elongated part extending distally from the tubular end part, and wherein the elongated part comprises a longitudinally extending groove configured to receive the guide rib.

8. The medical device of claim 1, wherein the proximal portion of the camera housing comprises a proximal end, a distal end and a tapering part between the proximal end and the distal end, wherein an outer diameter of the proximal end is smaller than an outer diameter of the distal end, wherein the inner face of the singular housing element comprises a guide rib, wherein the support structure comprises an elongated part extending distally from the tubular end part, the elongated part comprising a longitudinally extending groove configured to receive the guide rib.

9. The medical device of claim 1, wherein the outer face of the tubular end part of the support structure comprises pivot forming ribs, and wherein a plane traversing the pivot forming ribs also traverses the guide rib.

10. A visualization system comprising the medical device of claim 1 and a monitor or image display device, the medical device further comprising an image transmission cable, the monitor or image display device connected to the image transmission cable directly or via a wireless connection.

11. The visualization system of claim 10, wherein the outer wall further comprises an inner surface and an outer surface, the camera lumen formed in the outer wall between the inner surface and the outer surface.

12. The visualization system of claim 11, wherein the tube comprises a second lumen and a partition wall separating the first lumen and the second lumen, and wherein the camera lumen is formed an intersection of the outer wall and the partition wall.

13. The visualization system of claim 12, wherein the camera assembly includes a lens barrel having a central axis, and wherein the central axis is closer to the first lumen than to the second lumen.

14. A medical device including:
    a tube having an outer wall, a first lumen and a camera lumen, the first lumen having a proximal end and a distal end, the camera lumen having a proximal end and a distal end, and the outer wall enclosing the first lumen and the camera lumen;
    a camera housing including a proximal portion and a singular housing element affixed to the proximal portion, the singular housing element comprising a tubular housing part integrally moulded in one-piece with a distal end wall, the tubular housing part sized to fit tightly into the camera lumen of the tube, the tubular housing part having an inner face, a proximal end and a distal end;

a support structure positioned in the camera housing and comprising a proximal end, a distal end, and a tubular end part at the proximal end of the support structure, the tubular end part having an outer face forming a gap with the inner face of the tubular housing part;

an adhesive in the gap affixing the support structure to the singular housing element; and a camera module supported by the support structure inside the camera housing, the camera module including an image sensor and a light source positioned at the distal end of the camera lumen adjacent the distal end of the first lumen, wherein the outer face of the tubular end part of the support structure and/or the inner face of the tubular housing part of the camera housing are/is provided with ribs, and wherein the ribs include two pivot forming ribs arranged diametrically opposite of the tubular end part of the support structure and/or of the tubular housing part of the camera housing and together providing a pivot fit with the corresponding outer face or inner face, and wherein the ribs further include two distance ribs distributed peripherally about the tubular end part of the support structure and/or of the tubular housing part of the camera housing and together providing a distance fit with the corresponding outer face or inner face.

15. The medical device of claim 14, wherein the ribs only extend at a distal end of the tubular end part of the support structure.

16. The medical device of claim 14, wherein the two pivot forming ribs extend further radially than the two distance ribs.

17. The medical device of claim 14, wherein the distance fit is looser than the pivot fit.

18. The medical device of claim 17, wherein the distal end of the support structure is provided with two spaced tabs arranged generally symmetrically about a plane extending through the two pivot forming ribs, and wherein the two spaced tabs are adapted to abut the camera module.

19. The medical device of claim 18, wherein the support structure includes an elongated part having generally semicircular cross-section, and wherein the elongated part connects the proximal end of the support structure with the two spaced tabs.

20. The medical device of claim 19, wherein the elongated part is provided with a peripherally extending recess facing the inner face of the tubular part of the camera housing next to the tubular end part of the support structure.

21. The medical device of claim 19, wherein the inner face of the tubular part of the camera housing is provided with a guide rib, wherein the elongated part is provided with the groove extending in the longitudinal direction of the camera housing, wherein the groove is arranged symmetrically about the plane extending through the two pivot forming ribs.

22. The medical device of claim 14, wherein the recess comprises a through-hole.

23. A medical device including:

a tube having an outer wall, a first lumen and a camera lumen, the first lumen having a proximal end and a distal end, the camera lumen having a proximal end and a distal end, and the outer wall enclosing the first lumen and the camera lumen;

a camera housing including a proximal portion and a singular housing element affixed to the proximal portion, the singular housing element comprising a tubular housing part integrally molded in one-piece with a distal end wall, the tubular housing part sized to fit tightly into the camera lumen of the tube, the tubular housing part having an inner face, a proximal end and a distal end;

a support structure positioned in the camera housing and comprising a proximal end, a distal end, a tubular end part at the proximal end of the support structure, the tubular end part having an outer face forming a gap with the inner face of the tubular housing part;

an adhesive in the gap affixing the support structure to the singular housing element; and a camera module supported by the support structure inside the camera housing, the camera module including an image sensor and a light source positioned at the distal end of the camera lumen adjacent the distal end of the first lumen, wherein the support structure or the inner face of the tubular housing part of the camera housing has a guide rib extending in a longitudinal direction of the camera housing, wherein the corresponding support structure or inner face of the tubular housing part of the camera housing has a groove extending in the longitudinal direction of the camera housing, and wherein the guide rib is adapted to slide in the groove.

24. The medical device of claim 23, wherein the inner face of the tubular housing part of the camera housing is provided with the guide rib, and wherein the guide rib is wedge-formed at the distal end of the camera housing to guide the camera module during assembly.

25. A medical device including:

a tube having an outer wall, a first lumen and a camera lumen, the first lumen having a proximal end and a distal end, the camera lumen having a proximal end and a distal end, and the outer wall enclosing the first lumen and the camera lumen;

a camera housing including a proximal portion and a singular housing element affixed to the proximal portion, the singular housing element comprising a tubular housing part integrally molded in one-piece with a distal end wall, the tubular housing part sized to fit tightly into the camera lumen of the tube, the tubular housing part having an inner face, a proximal end and a distal end;

a support structure positioned in the camera housing and comprising a proximal end, a distal end, a tubular end part at the proximal end of the support structure, the tubular end part having an outer face forming a gap with the inner face of the tubular housing part;

an adhesive in the gap affixing the support structure to the singular housing element; and a camera module supported by the support structure inside the camera housing, the camera module including an image sensor and a light source positioned at the distal end of the camera lumen adjacent the distal end of the first lumen, the camera housing further comprising guide tabs provided on the inner face of the tubular housing part and/or on the distal end wall, and wherein the guide tabs are arranged to guide the camera module during its insertion into the camera housing.

26. A medical device including:

a tube having an outer wall, a first lumen and a camera lumen, the first lumen having a proximal end and a distal end, the camera lumen having a proximal end and a distal end, and the outer wall enclosing the first lumen and the camera lumen;

a camera housing including a proximal portion and a singular housing element affixed to the proximal portion, the singular housing element comprising a tubular housing part integrally moulded in one-piece with a distal end wall, the tubular housing part sized to fit tightly into the camera lumen of the tube, the tubular housing part having an inner face, a proximal end and a distal end;

a support structure positioned in the camera housing and comprising a proximal end, a distal end, and a tubular end part at the proximal end of the support structure, the tubular end part having an outer face forming a gap with the inner face of the tubular housing part;

an adhesive in the gap affixing the support structure to the singular housing element; and a camera module supported by the support structure inside the camera housing, the camera module including an image sensor and a light source positioned at the distal end of the camera lumen adjacent the distal end of the first lumen, wherein the outer wall further comprises an inner surface and an outer surface, the camera lumen formed in the outer wall between the inner surface and the outer surface, wherein the outer face of the tubular end part of the support structure and/or the inner face of the tubular housing part of the camera housing are/is tapered or conical so that the gap has a cross-section that decreases in the direction from the proximal end to the distal end of the support structure, and wherein the outer face of the tubular end part of the support structure and/or the inner face of the tubular housing part of the camera housing are/is provided with ribs including two pivot forming ribs and two distance ribs, the two pivot forming ribs arranged diametrically opposite of the tubular end part of the support structure and/or of the tubular part of the camera housing, the two distance ribs distributed peripherally about the tubular end part of the support structure and/or of the tubular part of the camera housing, the two pivot forming ribs extending radially further than the distance ribs.

\* \* \* \* \*